(12) United States Patent
Bridon et al.

(10) Patent No.: US 7,268,113 B2
(45) Date of Patent: Sep. 11, 2007

(54) LONG LASTING GROWTH HORMONE RELEASING FACTOR DERIVATIVES

(75) Inventors: Dominique P. Bridon, Ville Mont-Royal (CA); Nissab Boudjellab, Dorval (CA); Roger Léger, St-Lambert (CA); Martin Robitaille, Granby (CA); Lucie Jetté, Montreal (CA); Corinne Benquet, Laval (CA)

(73) Assignee: ConjuChem Biotechnologies Inc., Montreal (CA)

( * ) Notice: Subject to any disclaimer, the term of this patent is extended or adjusted under 35 U.S.C. 154(b) by 191 days.

(21) Appl. No.: 10/203,809

(22) PCT Filed: Feb. 1, 2002

(86) PCT No.: PCT/CA02/00123

§ 371 (c)(1),
(2), (4) Date: Aug. 12, 2002

(87) PCT Pub. No.: WO02/062844

PCT Pub. Date: Aug. 15, 2002

(65) Prior Publication Data

US 2003/0073630 A1 Apr. 17, 2003

(51) Int. Cl.
*A61K 38/18* (2006.01)
*C07K 14/475* (2006.01)

(52) U.S. Cl. .................................. 514/12; 530/324
(58) Field of Classification Search ............... 514/12; 530/324
See application file for complete search history.

(56) References Cited

U.S. PATENT DOCUMENTS

| | | | |
|---|---|---|---|
| 4,411,890 A | 10/1983 | Momany | 424/177 |
| 4,462,941 A | 7/1984 | Lee et al. | 206/112.5 R |
| 4,517,181 A | 5/1985 | Ling et al. | 514/12 |
| 4,518,586 A | 5/1985 | Rivier et al. | |
| 4,528,190 A | 7/1985 | Vale, Jr. et al. | |
| 4,529,595 A | 7/1985 | Rivier et al. | |
| 4,563,352 A | 1/1986 | Rivier et al. | |
| 4,585,756 A | 4/1986 | Brazeau, Jr. et al. | |
| 4,595,676 A | 6/1986 | Spiess et al. | |
| 4,605,643 A | 8/1986 | Bohlen et al. | |
| 4,610,976 A | 9/1986 | Bohlen et al. | |
| 4,626,523 A | 12/1986 | Vale, Jr. et al. | |
| 4,628,043 A | 12/1986 | Spiess et al. | |
| 4,689,318 A | 8/1987 | Kaiser et al. | |
| 4,734,399 A | 3/1988 | Felix et al. | |
| 4,784,987 A | 11/1988 | Rivier et al. | |
| 4,843,064 A | 6/1989 | Vaughan et al. | |
| 4,963,529 A | 10/1990 | Fujioka et al. | 514/12 |
| 5,416,073 A * | 5/1995 | Coy et al. | 514/12 |
| 5,493,007 A | 2/1996 | Burnier et al. | 530/317 |
| 5,580,853 A | 12/1996 | Sytkowski | 514/8 |
| 5,612,034 A | 3/1997 | Pouletty et al. | 424/184.1 |
| 5,654,276 A | 8/1997 | Barrett et al. | 514/13 |
| 5,756,458 A | 5/1998 | Kubiak et al. | |
| 5,843,440 A | 12/1998 | Pouletty et al. | 424/133.1 |
| 5,846,936 A * | 12/1998 | Felix et al. | 514/12 |
| 6,103,233 A | 8/2000 | Pouletty et al. | 424/133.1 |
| 6,184,201 B1 | 2/2001 | Summer-Smith et al. | |
| 6,204,054 B1 | 3/2001 | Sutton et al. | |

FOREIGN PATENT DOCUMENTS

| | | |
|---|---|---|
| DE | 4122210 | 1/1993 |
| DK | WO98/08872 | * 3/1998 |
| EP | 0188214 | 7/1986 |
| EP | 0602290 | 4/1994 |
| WO | 89/07110 | 8/1989 |
| WO | 89/07111 | 8/1989 |
| WO | WO 91/08220 | 6/1991 |
| WO | 92/18531 | 11/1992 |
| WO | 93/04081 | 3/1993 |
| WO | 93/25217 | 12/1993 |
| WO | 95/10302 | 4/1995 |
| WO | 96/06626 | 3/1996 |
| WO | 97/24445 | 7/1997 |
| WO | 98/08872 | 3/1998 |
| WO | 99/24075 | 5/1999 |
| WO | 99/24462 | 5/1999 |
| WO | 99/48536 | 9/1999 |
| WO | 00/69900 | 11/2000 |
| WO | 00/69911 | 11/2000 |
| WO | 00/76550 | 12/2000 |
| WO | 00/76551 | 12/2000 |
| WO | 01/68142 | 9/2001 |
| WO | WO 2005/099768 | 10/2005 |

OTHER PUBLICATIONS

Proceedings of the 8th American Peptide Symposium, 1983, 409-412.
Biotech Report, 1994/1995, 106-107.
Int. J. Biochem. Cell. Biol., 1998, 30, 1281-1284.
Endocrinology, 1982, 110 (3), 1049-1051.
J. Biol. Chem., 1995, 270 (43), 25344-25347.
J. Dev. Physiol., 1989, 12, 55-62.
Anti-Cancer Drugs, 1997, 8, 677-685.
Biopolymers (Peptide Science), 1998, 47, 451-463.

(Continued)

*Primary Examiner*—Cecilia Tsang
*Assistant Examiner*—Roy Teller
(74) *Attorney, Agent, or Firm*—Jones Day

(57) ABSTRACT

This invention relates to growth hormone releasing factor (GRF) derivatives. In particular, this invention relates to GRF peptide derivatives having an extended in vivo half-life, for promoting the endogenous production or release of growth hormone in humans and animals.

20 Claims, 5 Drawing Sheets

OTHER PUBLICATIONS

Ann. Rev. Neurosci., 1984, 7, 223-255.
Chem. Pharm. Bull., 1979, 27 (8), 1942-1944.
Proc. Natl. Acad. Sci., 1986, 83, 265-269.
TINS, 1993, 16, 403-409.
Biochem. and Biophysical Research Communications, 1984, 119 (1), 265-272.
American Journal of Physiology, Endocrinology and Metabolism, 2000, 278(1), E134-E139.
Nature Biotechnology, Nature Publishing, 1997, 15(7), 673-677.
Regulatory Peptides, 2000, 90(1-3), 27-32.
Trends in Endocrinology and Metabolism, 2000, 11(10), 401-405.
Endocrinology, 2001, 142(2), 521-527.
Kubiak, T. et al., Journal of Medicinal Chemistry, 1993, 36 (7), 888-897.
Campbell, R.M. et al., Journal of Peptide Research, 1997, 49 (6), 527-537.
Paige et al. "Prolonged circulation of recombinant human granulocyte-colony stimulating factor by covalent linkage to albumin through a heterobifunctional polyethylene glycol." Pharm Res. Dec. 1995; 12(12):1883-8.
Poznansky et al. "Growth hormone-albumin conjugates. Reduced renal toxicity and altered plasma clearance." FEBS Lett. Oct. 24, 1988;239(1):18-22.
International Search Report for International Application No. PCT/CA02/00123.

* cited by examiner

LONG LASTING GROWTH HORMONE RELEASING FACTOR DERIVATIVES

FIELD OF INVENTION

This invention relates to growth hormone releasing factor (GRF) derivatives. In particular, this invention relates to GRF peptide derivatives having an extended in vivo half-life, for promoting the endogenous production or release of growth hormone in humans and animals.

BACKGROUND OF THE INVENTION

Growth hormone (GH), also known as somatotropin, is a protein hormone of about 190 amino acids synthesized and secreted by cells called somatotrophs in the anterior pituitary. It is a major participant in control of growth and metabolism. It is also of considerable interest as a pharmaceutical product for use in both humans and animals. The production of GH is modulated by many factors, including stress, nutrition, sleep and GH itself. However, its primary controllers are two hypothalamic hormones:

the growth hormone-releasing factor (GRF or GHRH), a 44 amino acid sequence that stimulates the synthesis and secretion of GH and;

somatostatin (SS), which inhibits GH release in response to GRF.

It has been shown that the biological activity of GRF (1–44) resides in the N-terminal portion of the peptide. Full intrinsic activity and potency was also demonstrated with GRF (1–29) both in vitro and in vivo. Furthermore, sustained administration of GRF induces the same episodic secretory pattern of GH from the pituitary gland as under normal physiological conditions. Synthetic peptides such as growth hormone releasing peptide (GHRP) as well as peptidomimetics recently developed by Merck and other pharmaceutical companies have demonstrated their capability for stimulating the release of endogenous GH. Another analog a trisubstituted $GRF_{1-29}$ developed by Hoffmann-La Roche in the mid-80's, [des-amino-$Tyr^1$,D-$Ala^2$,$Ala^{15}$]-$GRF_{1-29}$, is a GRF superagonist with a prolonged duration of action.

GH secretagogues (GHSs) are known to stimulate the release of GH from the pituitary through an orphan G-protein-coupled receptor (GHS-R). Recently, another endogenous ligand for GHS-R was identified as ghrelin. It is an octanoylated (28-residue peptide with the n-octanoyl at $Ser^3$) peptide.

Recombinant GH (rGH) was first produced in 1985 and is now commercially available for both medical and veterinary uses. However, the long-term safety of rGH has not yet been determined. Further, several side effects resulting from the use of rGH in human have been reported, i.e., left ventricular mass index, an increase in serum lipoprotein, and a subtle change in immune parameters. Finally, frequent bolus injections of rGH are known to cause a progressive down-regulation of receptors, and thus to a decrease of its efficacy over time.

Besides these practical drawbacks, exogenous GH is species-specific, which limits its advantages in enhancing growth and other beneficial effects in different species, i.e. humans and animals. Small quantities of GRF have been found to cause substantial pituitary release of GH into the blood of treated animals. Thus GRF has great therapeutic utility in those instances where growth hormone is indicated. For example, it may be used in the treatment of hypopituitary dwarfism, diabetes due to GH production abnormalities, and retardation of the aging process. Many other diseases or conditions benefiting from endogenous production or release of GRF are enumerated below. Further, GRF is useful in the field of agriculture. Examples of agricultural uses include enhanced meat production of pigs, cattle or the like to permit earlier marketing. GRF is also known to stimulate milk production in dairy cows.

Up to now, a major drawback associated with the use of peptide-related GH secretagogues is the lack of a suitable technology capable of providing a substantially linear and sustained delivery of GH over prolonged periods of time, e.g., several days to weeks.

GRF (1–29), like many other peptides possessing therapeutic properties, is highly unstable in vivo, which significantly limits its use as pharmaceutical product to promote the release of GH in humans and animals. Because the half-life of GRF 1–29 generally does not exceed 10–13 minutes, it has to be injected in bolus several times a day or infused to be able to sustain measurable GH release.

Significant research efforts have been deployed over the past several years to develop long-acting analogs of GRF. Although several new analogs with improved duration of action have been synthesized, none of them meets the criteria that are required for GH-releasing drugs. Furthermore, no formulation is known to releasing such unstable peptides over a defined period of time in animals or humans.

U.S. Pat. No. 5,846,936 discloses GRF analogs that are said to have enhanced potency, increased enzyme stability and improved half-life stability. The patent mentions that the analogs can be administered with various adjuvants such as serum albumin. The only half-life stability results presented in the patent are in vitro. There is no data on the actual stability of the peptides in vivo.

U.S. Pat. No. 4,963,529 describes a GRF composition, either in the solid or liquid form, comprising GRF and human serum albumin or glycine. The composition may also contain a buffer, and is said to stabilize GRF.

WO 9724445 discloses the fusion of a growth hormone (hGH) with a molecule of recombinant albumin. Such fusion protein is said to have an increased circulatory half-life over unfused growth hormone. A linker, optionally cleavable, may be inserted between the molecule of albumin and the growth hormone, to facilitate binding of the hGH to the receptor.

WO 0069900 discloses a method for the production of peptidase-stabilized peptides. A series of GRF peptides are listed as potential candidates that can be stabilized according to the method disclosed in this application, but none of them are specifically exemplified in the description.

There is therefore a great need to develop a long-lasting compound capable of promoting the release of GH in a subject, animal or human. Such promotion should preferably be sustained over an extended period of time without the undesirable side effects of rGH.

SUMMARY OF THE INVENTION

In accordance with the present invention, there is now provided a growth hormone releasing factor (GRF) derivative having an extended in vivo half-life when compared to the corresponding unmodified (or native) GRF peptide sequence. More specifically, the derivative comprises a GRF peptide or an analog thereof comprising a reactive entity coupled thereto and capable of reacting with available functionalities on a blood component, either in vivo or ex vivo, to form a stable covalent bond. The reactive entity may be coupled to the N-terminal of the peptide, the C-terminal of the peptide, or to any other available site along the peptidic chain.

Preferred blood components comprise proteins such as immunoglobulins, including IgG and IgM, serum albumin, ferritin, steroid binding proteins, transferrin, thyroxin binding protein, α-2-macroglobulin etc., serum albumin and IgG being more preferred, and serum albumin being the most preferred.

Preferred reactive entities are capable of forming a covalent bond with the blood component by reacting with amino groups, hydroxy groups or thiol groups present thereon, either in vivo or in vitro (or ex vivo). In a most preferred embodiment, the functionality on the protein will be a thiol group and the reactive entity will be a Michael acceptor, such as acrolein derivatives, α,β-unsaturated ketones, α,β-unsaturated esters, α,β-unsaturated amides, α,β-unsaturated thioesters, and the like, maleimide or maleimido-containing group such as γ-maleimide-butyrylamide (GMBA) or maleimidopropionic acid (MPA) being the most preferred.

In another aspect of the invention, there is provided a pharmaceutical composition comprising the present GRF derivative in combination with a pharmaceutically acceptable carrier. Such composition is useful for the promotion of endogenous GH production or release in a subject. The composition may also be used for the manufacture of pharmaceutical or veterinary compositions for treating or preventing diseases or conditions resulting from GH production abnormalities. A list of such diseases or conditions appears below.

In a further embodiment of the present invention, there is provided a method for promoting the endogenous production or release of GH in a subject, animal or human. The method comprises administering to the subject, an effective amount of the present GRF derivative, alone or in combination with a pharmaceutical carrier.

In a further embodiment of the present invention, there is provided a method for treating or preventing diseases or conditions resulting from GH production abnormalities, comprising administering to the subject, an effective amount of the present GRF derivative, alone or in combination with a pharmaceutical carrier.

In a further aspect of the present invention, there is provided a conjugate comprising the present GRF derivative covalently bonded to a blood component.

In a further aspect of the present invention, there is provided a method for extending the in vivo half-life of a GRF peptide in a subject, the method comprising covalently bonding the present GRF derivative to a blood component. The covalent bonding may take place in vivo or in vitro.

In a further aspect of the present invention, there is provided a method for treating or preventing diseases or conditions resulting from GH production abnormalities, comprising administering to a subject an effective amount of the present conjugate, alone or in combination with a pharmaceutical carrier.

Preferred GRF are peptides such as GRF (1–44) and analogs thereof such as GHRP-6, Hexarelin, Ghrelin, GHRP-1, IGF-1, IGF-2, B-HT920, GRF (1–29), and analogs and fragments thereof, as enumerated below, provided that such any analog or fragment possesses activity substantially similar to that of GRF. U.S. Pat. Nos. 4,411,890; 4,517,181; 4,518,586; 4,528,190; 4,529,595; 4,563,352; 4,585,756; 4,595,676; 4,605,643; 4,610,976; 4,626,523; 4,628,043; 4,689,318; 4,734,399; 4,784,987; 4,843,064; 5,756,458; EP 0 188 214; WO 89/07110; WO 89/07111 and WO 93/04081, all of which being hereby incorporated by reference, provide additional GRF analogs suitable for derivatization in accordance with the present invention.

If a linking group is present between the reactive entity and the GRF peptide, it is preferably defined as, without limitation, a straight or branched $C_{1-10}$ alkyl; a straight or branched $C_{1-10}$ alkyl partly or perfluorinated; a $C_{1-10}$ alkyl or fluoroalkyl wherein one or more carbon atom is replaced with O or S to form an ether or a thioether, for example, -Z-CH$_2$CH$_2$—, -Z-CF$_2$CH$_2$—, -Z-CH$_2$CF$_2$— or -Z-CF$_2$—CF$_2$— wherein Z is O or S; o-, m- or p-disubstituted phenyl wherein the substituents are the same or different and are CH$_2$, O, S, NH, NR wherein R is H, $C_{1-10}$ alkyl or $C_{1-10}$ acyl; or disubstituted heterocycles such as furan, thiophene, pyran, oxazole, or thiazole.

IN THE DRAWINGS

DETAILED DESCRIPTION OF THE INVENTION

Figure 1:
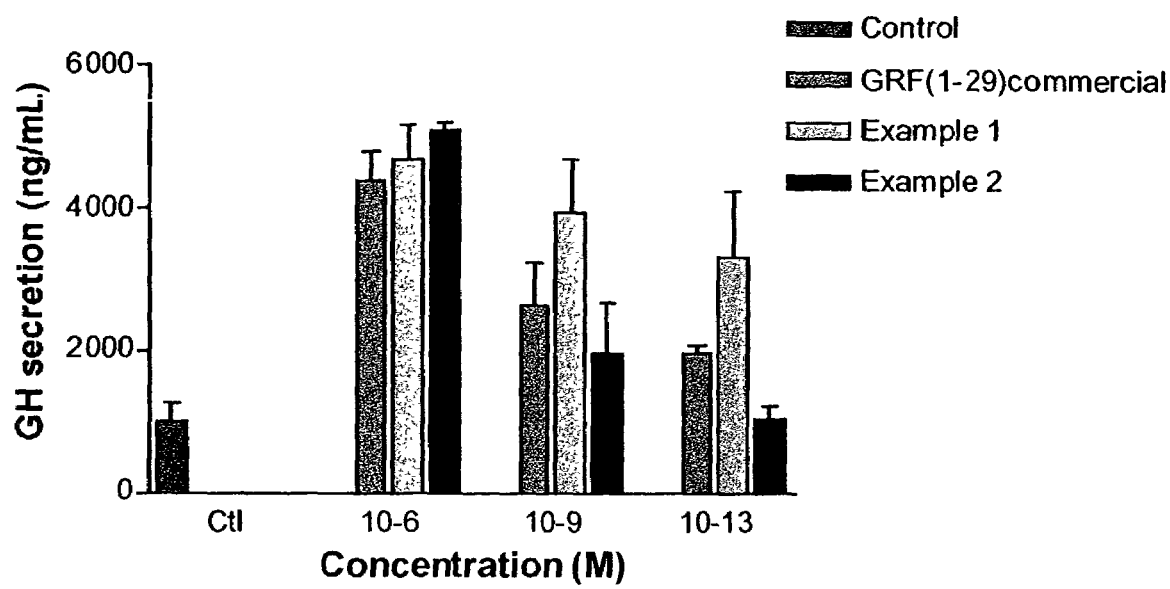
FIG. 1 illustrates GH secretion from rat anterior primary cells following a four hours incubation with commercial GRF (1–29) and the compounds of Examples 1 and 2 at various concentrations.
Figure 2:
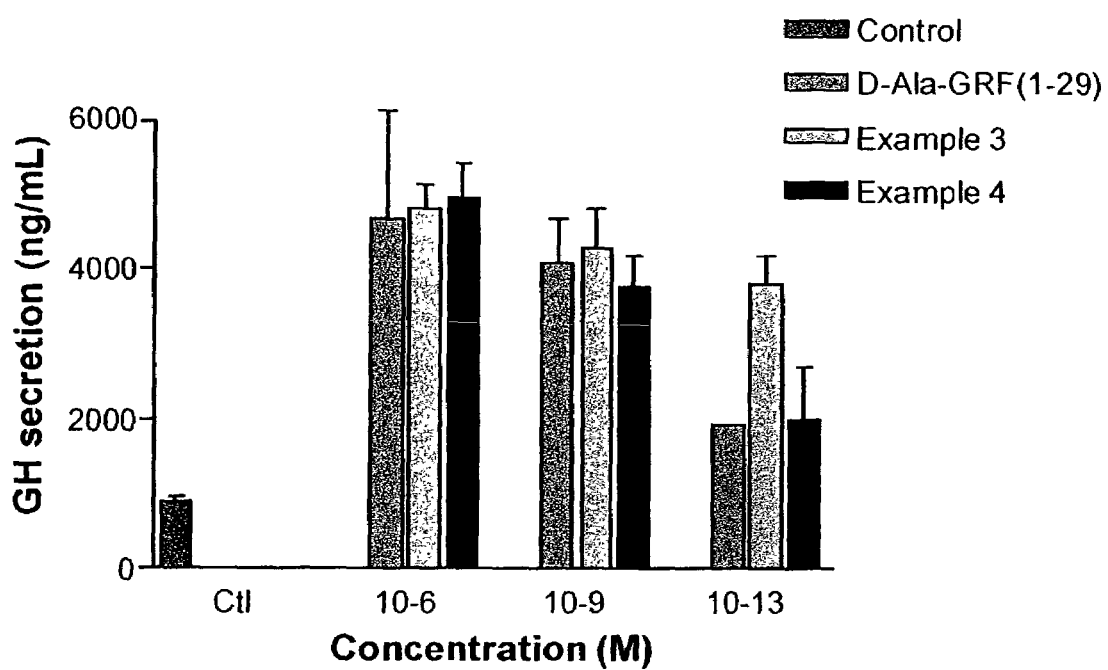
FIG. 2 illustrates GH secretion from rat anterior primary cells following a four hours incubation with commercial D-Ala-GRF (1–29) and the compounds of Examples 3 and 4 at various concentrations.
Figure 3:
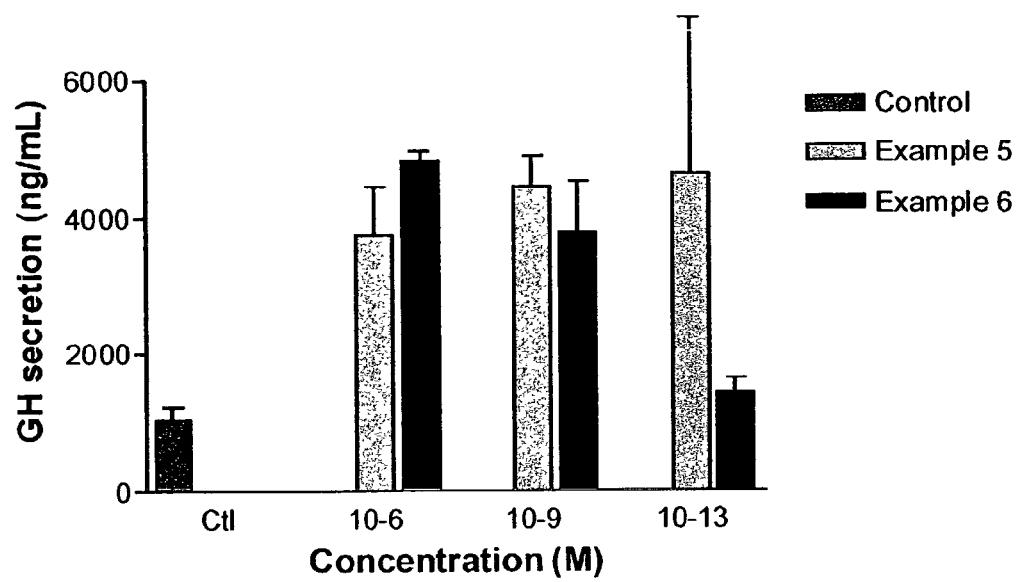
FIG. 3 illustrates GH secretion from rat anterior primary cells following a four hours incubation with the compounds of Examples 5 and 6 at various concentrations.
Figure 4:
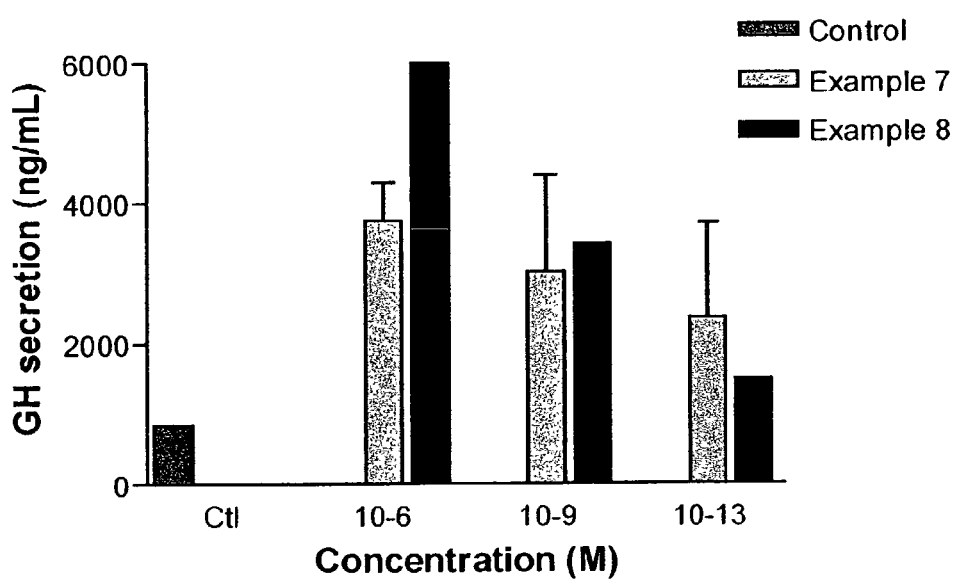
FIG. 4 illustrates GH secretion from rat anterior primary cells following a four hours incubation with the compounds of Examples 7 and 8 at various concentrations.
Figure 5:
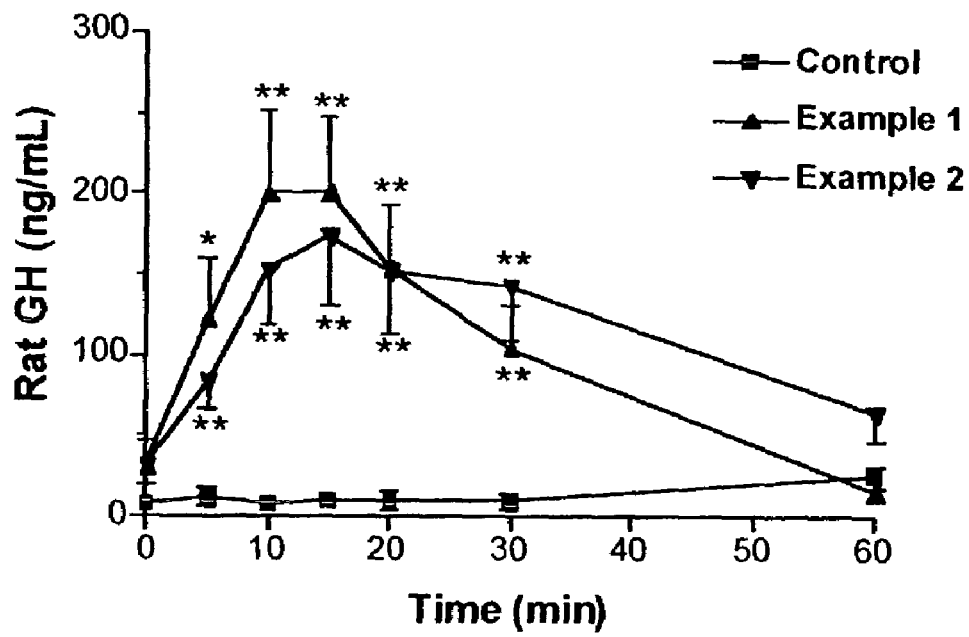
FIG. 5 illustrates GH secretion in normal Sprague-Dawley rats following a single subcutaneous bolus injection of the compounds of Examples 1 and 2.
Figure 6:
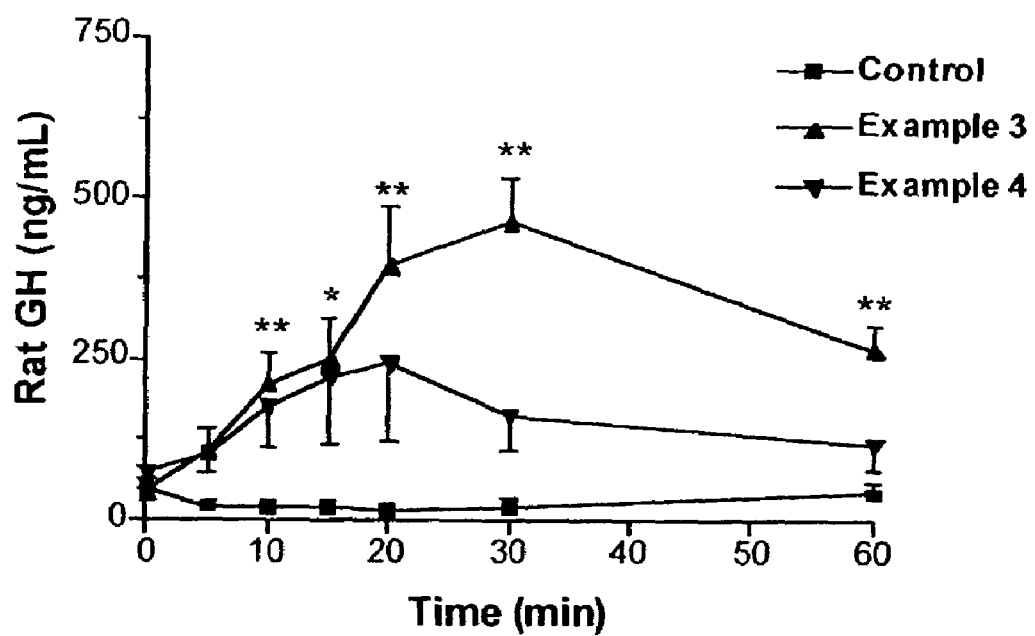
FIG. 6 illustrates GH secretion in normal Sprague-Dawley rats following a single subcutaneous bolus injection of the compounds of Examples 3 and 4.
Figure 7:
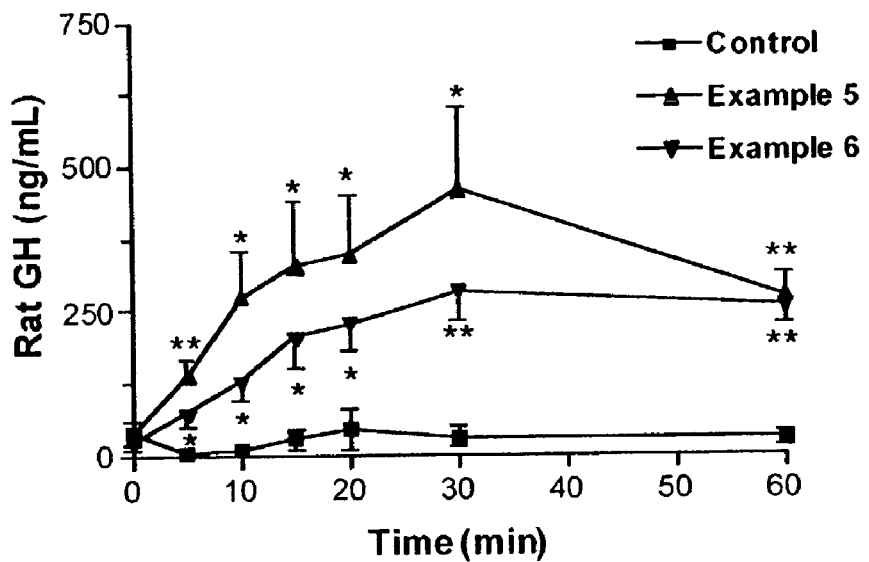
FIG. 7 illustrates GH secretion in normal Sprague-Dawley rats following a single subcutaneous bolus injection of the compounds of Examples 5 and 6.
Figure 8:
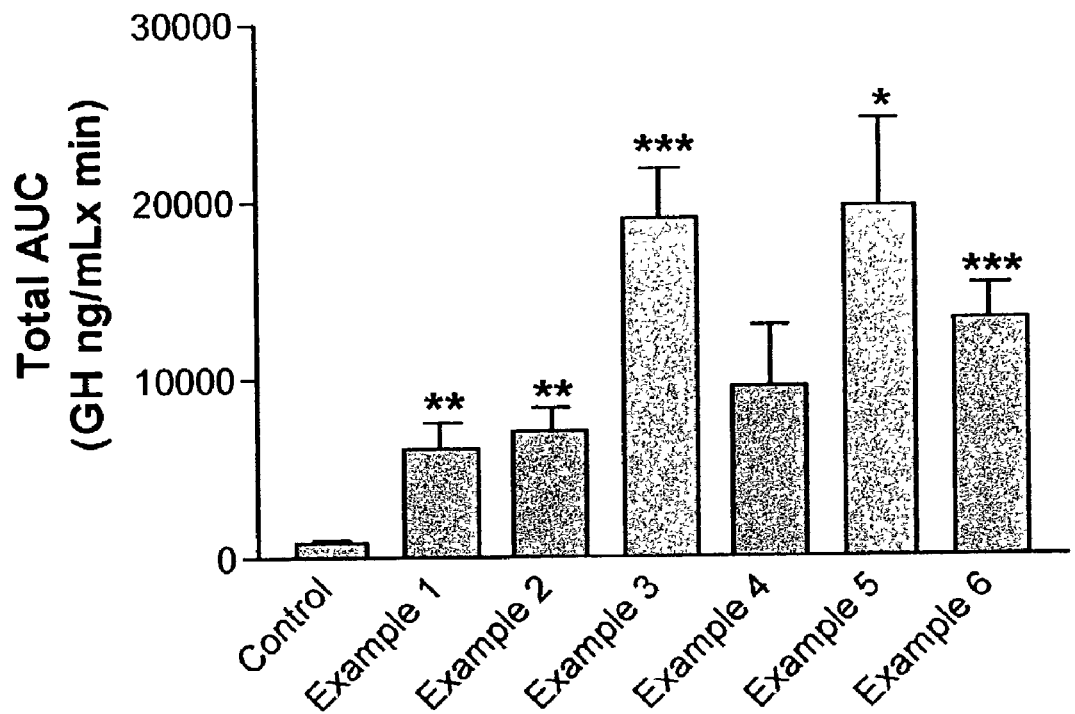
FIG. 8 illustrates GH secretion (Total Area Under the curve; AUC) in normal Sprague-Dawley rats following a single subcutaneous bolus injection.

In vivo bioconjugation is the process of covalently bonding a molecule, such as the present GRF derivative, within the body, to target blood components, preferably proteins, in a manner that permits the substantial retention of the biological activity of the original unmodified GRF therein, while providing an extended duration of the biological activity though giving the GRF derivative the biophysical parameters of the target blood component.

For the purposes of the present invention, the term "analog" is meant to include amino acid sequences comprising peptides with different amino acid sequences from the native GRF sequence but with similar or comparable activity. Such analogs preferably have an amino acid sequence at least 60%, and more preferably at least 80%, and most preferably at least 95% the same as that of either GRF or a fragment of GRF having the same number of amino acid residues.

In a more preferred embodiment, the present GRF derivative comprises a GRF peptide that has been modified by coupling thereto a reactive entity, either directly or via a linking group, the reactive entity being capable of forming a covalent bond with a blood component, preferably blood proteins. The reactive entity must be stable in an aqueous environment, and preferred embodiments thereof comprise carboxy group, a phosphoryl group, an imidate group, or an acyl group either as an ester or a mixed anhydride. The covalent bond is generally formed between the reactive entity and an amino group, a hydroxy group, or a thiol group on the blood component. The amino group preferably forms a covalent bond with reactive entities like carboxy, phosphoryl or acyl; the hydroxy group preferably forms a covalent bond with reactive entities like activated esters; and the thiol group preferably forms a covalent bond with reactive entities like esters or mixed anhydrides. The preferred blood component comprises mobile blood components like serum albumin, immunoglobulins, or combinations thereof, and the preferred reactive entity comprises anhydrides like maleimide groups. In a most preferred embodiment, the blood component is serum albumin.

The blood components are preferably mobile, which means that they do not have a fixed situs for any extended period of time, generally not exceeding 5 minutes, and more usually one minute. These blood components are not membrane-associated and are present in the blood for extended periods of time in a minimum concentration of at least 0.1 µg/ml. Preferred mobile blood components include serum albumin, transferrin, ferritin and immunoglobulins such as IgM and IgG. The half-life of mobile blood components is at least about 12 hours.

Because the present GRF derivative comprises a peptide, protective groups may be required during the synthesis process of the derivative. These protective groups are conventional in the field of peptide synthesis, and can be generically described as chemical moieties capable of protecting the peptide derivative from reacting with itself. Various protective groups are available commercially, and examples thereof can be found in U.S. Pat. No. 5,493,007 which is hereby incorporated by reference. Typical examples of suitable protective groups include acetyl, fluorenylmethyloxycarbonyl (FMOC), t-butyloxycarbonyl (BOC), benzyloxycarbonyl (CBZ), etc. Table 1 provides both the three letter and one letter abbreviations for amino acids.

TABLE 1

NATURAL AMINO ACIDS AND THEIR ABBREVIATIONS

| Name | 3-letter abbreviation | 1-letter abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |

TABLE 1-continued

NATURAL AMINO ACIDS AND THEIR ABBREVIATIONS

| Name | 3-letter abbreviation | 1-letter abbreviation |
| --- | --- | --- |
| Tryptophan | Trp | W |
| Tyrosine | Tyr | Y |
| Valine | Val | V |

The present GRF derivative forms a peptidase-stabilized long lasting compound after conjugation to a blood component. It is also contemplated that one or more additional amino acids may be added to the peptide prior to addition of the reactive entity, to facilitate the coupling thereof to the peptide. Such addition may be made at the C-terminal, the N-terminal, or therebetween. The thus obtained peptide derivative may be administered to a subject, animal or human, such that conjugation with blood components occurs in vivo, or they may be first conjugated to blood components of the subject, animal or human, in vitro, and the resulting conjugate, or long lasting peptidase-stabilized peptide derivative as defined below, administered to the subject.

Any amino acid, present, substituted with or added to, the GRF sequence, may be D-amino acids or L-amino acids or combinations thereof. L-amino acids are generally preferred. The following substitutions or mutations within the native GRF peptide sequence (1–29) or (1–44) represent preferred embodiments of the invention, either independently or in combinations: D-alanine at position 2; glutamine at position 8; D-arginine at position 11; (N-Me) Lys at position 12; alanine at position 15; and leucine at position 27.

The invention also includes GRF fragments which, although containing a sequence that is substantially homologous to that of a naturally occurring GRF peptide, may lack one or more additional amino acids at their amino and/or their carboxy termini that are naturally found on a GRF native peptide. Thus, the invention pertains to polypeptide fragments of GRF that may lack one or more amino acids that are normally present in a naturally occurring GRF sequence provided that such polypeptides have growth hormone releasing activity which preferably at least substantially equals that of GRF.

The invention also encompasses the obvious or trivial variants of the above-described analogs or fragments which have inconsequential amino acid substitutions (and thus have amino acid sequences which differ from that of the natural sequence) provided that such variants have growth hormone releasing activity which is substantially similar to that of GRF. Examples of obvious or trivial substitutions include the substitution of one basic residue for another (i.e. Arg for Lys), the substitution of one hydrophobic residue for another (i.e. Leu for Ile), or the substitution of one aromatic residue for another (i.e. Phe for Tyr), etc. Further, other trivial variants include analogs wherein conservative substitutions resulting in a substantial structural analogy of the original sequence are obtained. Examples of such conservative substitutions, without limitation, include glutamic acid for aspartic acid and vice-versa; glutamine for asparagine and vice-versa; serine for threonine and vice-versa; lysine for arginine and vice-versa; or any of isoleucine, valine or leucine for each other.

A peptidase-stabilized GRF derivative is more stable in the presence of peptidases in vivo than the corresponding non-stabilized GRF analog. The peptidase stability is determined by comparing the half-life of the native GRF analog in serum or blood to the half-life of the corresponding derivative containing the reactive group in serum or blood. Half-life is determined by sampling the serum or blood after administration of the derivative and the non-modified peptide, and determining the activity of each compound.

In greater details, the present invention is directed to the modification of GRF and related peptides to improve its bioavailability, extend in vivo half-life and distribution through selective conjugation onto a blood component without substantially altering their remarkable therapeutic properties.

"In a more preferred embodiment, the GRF peptide sequence suitable for derivatization according to the present invention is of the following sequence:

$A_1$-$A_2$-Asp-$A_4$-Ile-Phe-$A_7$-$A_8$-$A_9$-Tyr-$A_{11}$-$A_{12}$-$A_{13}$-Leu-$A_{15}$-Gln-Leu-$A_{18}$-Ala-$A_{20}$-$A_{21}$-$A_{22}$-Leu-$A_{24}$-$A_{25}$-$A_{26}$-$A_{27}$-$A_{28}$-$A_{29}$-$A_{30}$ (SEQ ID NO: 1, SEQ ID NO: 7–13)

wherein, $A_1$ is Tyr, N-Ac-Tyr, His, 3-MeHis, desNH$_2$ His, desNH$_2$ Tyr, Lys-Tyr, Lys-His or Lys-3-MeHis;
$A_2$ is Val, Leu, Ile, Ala, D-Ala, N-methyl-D-Ala, (N-methyl)-Ala, Gly, Nle ou Nval;
$A_4$ is Ala or Gly;
$A_5$ is Met or Ile;
$A_7$ is Asn, Ser or Thr;
$A_8$ is Asn, Gln, Lys or Ser;
$A_9$ is Ala or Ser;
$A_{11}$ is Arg, D-Arg, Lys or D-Lys;
$A_{12}$ is Lys, (N-Me)Lys, or D-Lys;
$A_{13}$ is Val or Leu;
$A_{15}$ is Ala, Leu or Gly;
$A_{18}$ is Ser or Thr;
$A_{20}$ is Arg, D-Arg, Lys or D-Lys;
$A_{21}$ is Lys, (N-Me)Lys, or Asn;
$A_{22}$ is Tyr or Leu;
$A_{24}$ is Gln or His;
$A_{25}$ is Ser or Asp;
$A_{26}$ is Leu or Ile;
$A_{27}$ is Met, Ile, Leu or Nle;
$A_{28}$ is Ser, Asn, Ala or Asp;
$A_{29}$ is Lys or Arg; and
$A_{30}$ is absent, X, or X-Lys wherein X is absent or is the sequence Gln-Gln-Gly-Glu-Ser-Asn-Gln-Glu-Arg-Gly-Ala-Arg-Ala-Arg-Leu or a fragment thereof, wherein the fragment is reduced by one to fifteen amino acids from the C-terminal; and wherein one amino acid residue from the fragment can optionally be replaced with a lysine residue; and wherein the C-terminal can be the free carboxylic acid or the corresponding amide, with the proviso that if $A_2$ is Ala, then the fragment is not a fragment reduced by 5–8 amino acids.

The invention relates to therapeutic and related uses of GRF derivatives having an extended half-life in vivo, particularly for increasing the level of growth hormone;
diagnosing growth hormone deficiencies, by administering to the subject the present GRF derivative analog and measuring the growth hormone response;
treating pituitary dwarfism;
treating or preventing growth retardation;
accelerating bone fracture repair or wound healing;
accelerating the recovery of burn patients or patients who underwent major surgery;
improving muscle strength, mobility, maintenance of skin thickness, metabolic homeostasis or renal homeostasis;
treating or preventing congestive heart failure;
treating or preventing frailty associated with aging;
treating or preventing osteoporosis;
treating or preventing obesity,
attenuating protein catabolic response after major surgery;
reducing cachexia and protein loss due to chronic illness;
improving protein anabolism (including protein sparing effect);
inducing a lipolytic effect; and/or
upgrading the somatotroph function.

All the above methods can be applied either to humans or animals.

In addition to promoting endogenous production or release of growth hormone, the present GRF derivatives may incorporate an amino acid substitution at one or more sites within a GRF peptide "backbone", or is a variant of GRF species in which the C-terminal and/or the N-terminal has been altered by addition of one or more basic residues, or has been modified to incorporate a blocking group of the type used conventionally in the art of peptide chemistry to protect peptide termini from undesired biochemical attack and degradation in vivo. Thus, the present GRF derivatives incorporate an amino acid substitution in the context of any GRF species, including but not limited to human GRF, bovine GRF, rat GRF, porcine GRF etc., the sequences of which having been reported by many authors. In a more preferred embodiment, a lysine residue is added at the C-terminal or N-terminal of the GRF peptide sequence.

In a preferred embodiment, the functionality on the protein will be a thiol group and the reactive entity will be a maleimide or maleimido-containing group such as γ-maleimide-butyrylamide (GMBA), maleimidopropionic acid (MPA), (2-amino) ethoxy acetic acid (AEA)-MPA, ethylenediamine (EDA)-MPA or [2-(2-amino)ethoxy)]ethoxy acetic acid (AEEA)-MPA and combinations thereof. Examples of combinations include, without limitations, (AEEA-EDA)-MPA; (AEEA—AEEA)-MPA, (AEA-AEEA)-MPA and the like.

Maleimide groups are most selective for sulfhydryl groups on peptides when the pH of the reaction mixture is kept between 6.5 and 7.4. At pH 7.0, the rate of reaction of maleimido groups with sulfhydryls is 1000-fold faster than with amines. A stable thioether linkage between the maleimido group and the sulfhydryl is formed which cannot be cleaved under physiological conditions.

The GRF derivatives of the invention provide for specific labeling of blood components. Such specific labeling, particularly with a maleimide, offers several advantages. Thiol groups are less abundant in vivo than amino groups, and as a result, maleimide derivatives covalently bond to fewer proteins. For example, in serum albumin, there is only one free thiol group per molecule. Thus, a GRF-maleimide-albumin conjugate will tend to comprise approximately a 1:1 molar ratio of peptide to albumin. In addition to albumin, IgG molecules (class II) also have free thiols. Since IgG molecules and serum albumin make up the majority of soluble proteins in the blood, they also make up the majority of the free thiol groups available to covalently bond to a maleimide-substituted GRF.

Further, even among free thiol-containing blood proteins, specific labeling with a maleimide leads to the preferential formation of peptide maleimide-albumin conjugates, due to the unique characteristics of albumin itself. The single free thiol group of albumin, highly conserved among species, is located at amino acid residue $Cys_{34}$. It has been demonstrated recently that the $Cys_{34}$ of albumin has an increased reactivity relative to free thiols on other free thiol-containing proteins. This is due in part to the very low pK value of 5.5 for the $Cys_{34}$ of albumin. This is much lower than typical pK values for cysteines residues in general, which are typically about 8. Due to this low pK, under normal physiological conditions, $Cys_{34}$ of albumin is predominantly in the ionized form, which dramatically increases its reactivity. In addition to the low pK value of $Cys_{34}$, another factor which enhances the reactivity of $Cys_{34}$ is its location, which is in a crevice close to the surface of one loop of region V of albumin. This location makes $Cys_{34}$ very accessible to ligands of all kinds, and is an important factor in $Cys_{34}$'s biological role as free radical trap and free thiol scavenger. As a result, the reaction rate acceleration can be as much as 1000-fold relative to rates of reaction of peptide-maleimides with other free-thiol containing proteins.

Another advantage of peptide-maleimide-albumin conjugates is the reproducibility associated with the 1:1 loading of peptide to albumin specifically at $Cys_{34}$. Conventional activation techniques, such as with glutaraldehyde, DCC, EDC and other chemical activators of, for example, free amines, lack this selectivity. For example, albumin contains 52 lysine residues, 25–30 of which being located on the surface of albumin and accessible for conjugation. Activating these lysine residues, or alternatively modifying a peptide to couple through these lysine residues, results in a heterogeneous population of conjugates. Even if an equimolar ratio peptide:albumin (i.e., 1:1) is employed, the end result is the production of random conjugation products, some containing an indefinite number of peptides linked to each molecule of albumin, and each conjugate having peptides randomly coupled at any one of the 25–30 available lysine sites. Consequently, characterization of the exact composition is virtually impossible, not to mention the absence of reproducibility. Additionally, while it would seem that conjugation through lysine residues of albumin would at least have the advantage of delivering more therapeutic agent per albumin molecule, studies have shown that a 1:1 ratio of therapeutic agent to albumin is preferred. In an article by Stehle, et al. *Anti-Cancer Drugs,* 1997, 8, 677–685, which is incorporated herein in its entirety, it is reported that a 1:1 ratio of the anti-cancer methotrexate to albumin conjugated via glutaraldehyde gave the most promising results. These conjugates were taken up by tumor cells, whereas conjugates bearing 5:1 to 20:1 methotrexate molecules had altered HPLC profiles and were quickly taken up by the liver in vivo. It would therefore seem that at higher ratios, the conformational changes to albumin diminish its effectiveness as a carrier for a therapeutic agent.

Through controlled administration of the present GRF derivative, and particularly a GRF comprising a maleimide reactive entity, specific in vivo labeling or bonding of albumin and IgG can be controlled. In typical administrations, it has been shown that 80–90% of the administered peptide derivative bonds to albumin and less than 5% bonds to IgG. Trace bonding of free thiols present, such as glutathione, also occurs. Such specific bonding is preferred for in vivo use as it permits an accurate calculation of the estimated half-life of the therapeutic agent administered.

In addition to providing controlled specific in vivo bonding, maleimide-substituted GRF peptide can provide specific labeling of serum albumin and IgG ex vivo. Such ex vivo bonding involves the addition of maleimide-peptides to blood, serum or saline solution containing purified blood components such as serum albumin and/or IgG. In a preferred format, the derivative is substituted with a maleimide, optionally via a linking group, and it is reacted with human serum albumin in saline solution. Once modified ex vivo with the present GRF derivatives, the blood, serum or saline solution can be re-administered to the blood for in vivo treatment.

Maleimide-substituted GRF peptides are generally quite stable in the presence of aqueous solutions and in the presence of free amines. Because maleimide-substituted GRF peptides react with free thiols, protective groups are not necessary to prevent them from reacting with themselves. In addition, the increased stability of the peptide derivative permits the use of further purification steps such as HPLC to prepare highly purified products suitable for in vivo use. Lastly, the increased chemical stability provides a product with a longer shelf life.

The desired conjugates of GRF derivatives to blood components may be prepared in vivo by administration of the derivatives directly to the subject, which may be an animal or a human. The administration may be done in the form of a bolus, or introduced slowly over time by infusion using metered flow or the like.

Alternately, the conjugate may also be prepared ex vivo by combining blood or commercially available purified blood components with the present GRF derivative, allowing covalent bonding of the GRF derivative to the functionalities on blood components, and then returning or administering the conjugated blood or conjugated purified blood component to the host. Moreover, the above may also be accomplished by first purifying an individual blood component or limited number of components, such as red blood cells, immunoglobulins, serum albumin, or the like, and combining the component or components ex vivo with the present compound derivative. The labeled blood or blood component may then be returned to the subject to provide in vivo the therapeutically effective conjugates. The blood also may be treated to prevent coagulation during handling ex vivo.

Peptide Synthesis

GRF peptides may be synthesized by standard methods of solid phase peptide chemistry well known to any one of ordinary skill in the art. For example, the peptide may be synthesized by solid phase chemistry techniques following the procedures described by Steward et al. in *Solid Phase Peptide Synthesis,* 2nd Ed., Pierce Chemical Company, Rockford, Ill., (1984) using an Applied Biosystem synthesizer. Similarly, peptides fragments may be synthesized and subsequently combined or linked together to form a larger peptide. These synthetic peptide fragments can also be made with amino acid substitutions at specific locations.

For solid phase peptide synthesis, a summary of the many techniques may be found in Stewart et al. in "*Solid Phase Peptide Synthesis*", W. H. Freeman Co. (San Francisco), 1963 and Meienhofer, *Hormonal Proteins and Peptides,* 1973, 2 46. For classical solution synthesis, see for example Schroder et al. in "*The Peptides*", volume 1, Acacemic Press (New York). In general, such method comprises the sequential addition of one or more amino acids or suitably protected amino acids to a growing peptide chain. Normally, either the amino or carboxyl group of the first amino acid is protected by a suitable protecting group. The protected or derivatized amino acid is then either attached to an inert solid support or utilized in solution by adding the next amino acid in the sequence having the complementary (amino or carboxyl) group suitably protected and under conditions suitable for forming the amide linkage. The protecting group is then removed from this newly added amino acid residue and the next amino acid (suitably protected) is added, and so forth.

After all the desired amino acids have been linked in the proper sequence, any remaining protecting groups (and any solid support) are removed sequentially or concurrently to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing the present GRF derivatives involves solid phase peptide synthesis wherein the amino acid α-N-terminal is protected by an acid or base sensitive group. Such protecting groups should have the properties of being stable to the conditions of peptide linkage formation while being readily removable without destruction of the growing peptide chain or racemization of any of the chiral centers contained therein. Examples of N-protecting groups and carboxy-protecting groups are disclosed in Greene, "Protective Groups In Organic Synthesis," (John Wiley & Sons, New York pp. 152–186 (1981)), which is hereby incorporated by reference. Examples of N-protecting groups comprise, without limitation, loweralkanoyl groups such as formyl, acetyl ("Ac"), propionyl, pivaloyl, t-butylacetyl and the like; other acyl groups include 2-chloroacetyl, 2-bromoacetyl, trifluoroacetyl, trichloroacetyl, phthalyl, o-nitrophenoxyacetyl, -chlorobutyryl, benzoyl, 4-chlorobenzoyl, 4-bromobenzoyl, 4-nitrobenzoyl and the like; sulfonyl groups such as benzenesulfonyl, p-toluenesulfonyl, o-nitrophenylsulfonyl, 2,2,5,7,8-pentamethylchroman-6-sulfonyl (pmc), and the like; carbamate forming groups such as t-amyloxycarbonyl, benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-ethoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (boc), diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, isobornyloxycarbonyl, cyclopentyloxycarbonyl, adamantyloxycarbonyl, cyclohexyloxycarbonyl, phenylthiocarbonyl and the like; arylalkyl groups such as benzyl, biphenylisopropyloxycarbonyl, triphenylmethyl, benzyloxymethyl, 9-fluorenylmethyloxycarbonyl (Fmoc) and the like and silyl groups such as trimethylsilyl and the like. Preferred α-N-protecting group are o-nitrophenylsulfenyl; 9-fluorenylmethyloxycarbonyl; t-butyloxycarbonyl (boc), isobornyloxycarbonyl; 3,5-dimethoxybenzyloxycarbonyl; t-amyloxycarbonyl; 2-cyano-t-butyloxycarbonyl, and the like, 9-fluorenyl-methyloxycarbonyl (Fmoc) being more preferred, while preferred side chain N-protecting groups comprise 2,2,5,7,8-pentamethylchroman-6-sulfonyl (pmc), nitro, p-toluenesulfonyl, 4-methoxybenzene-sulfonyl, Cbz, Boc, and adamantyloxycarbonyl for side chain amino groups like lysine and arginine; benzyl, o-bromobenzyloxycarbonyl, 2,6-dichlorobenzyl, isopropyl, t-butyl (t-Bu), cyclohexyl, cyclopenyl and acetyl (Ac) for tyrosine; t-butyl, benzyl and tetrahydropyranyl for serine; trityl, benzyl, Cbz, p-toluenesulfonyl and 2,4-dinitrophenyl for histidine; formyl for tryptophan; benzyl and t-butyl for aspartic acid and glutamic acid; and triphenylmethyl (trityl) for cysteine.

A carboxy-protecting group conventionally refers to a carboxylic acid protecting ester or amide group. Such carboxy protecting groups are well known to those skilled in the art, having been extensively used in the protection of carboxyl groups in the penicillin and cephalosporin fields as described in U.S. Pat. Nos. 3,840,556 and 3,719,667, the disclosures of which are hereby incorporated herein by reference. Representative carboxy protecting groups comprise, without limitation, $C_1$–$C_8$ loweralkyl; arylalkyl such as phenethyl or benzyl and substituted derivatives thereof such as alkoxybenzyl or nitrobenzyl groups; arylalkenyl such as phenylethenyl; aryl and substituted derivatives thereof such as 5-indanyl; dialkylaminoalkyl such as dimethylaminoethyl; alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl; aroyloxyalkyl such as benzoyloxymethyl, benzoyloxyethyl; arylalkylcarbonyloxyalkyl such as benzylcarbonyloxymethyl, 2-benzylcarbonyloxyethyl; alkoxycarbonylalkyl or cycloalkyloxycarbonylalkyl such as methoxycarbonylmethyl, cyclohexyloxycarbonylmethyl, 1-methoxycarbonyl-1-ethyl; alkoxycarbonyloxyalkyl or cycloalkyloxycarbonyloxyalkyl such as methoxycarbonyloxymethyl, t-butyloxycarbonyloxymethyl, 1-ethoxycarbonyloxy-1-ethyl, 1-cyclohexyloxycarbonyloxy-1-ethyl; aryloxycarbonyloxyalkyl such as 2-(phenoxycarbonyloxy)ethyl, 2-(5-indanyloxycarbonyloxy)-ethyl; alkoxyalkylcarbonyloxyalkyl such as 2-(1-methoxy-2-methylpropan-2-oyloxy)-ethyl; arylalkyloxycarbonyloxyalkyl such as 2-(benzyloxycarbonyloxy)ethyl; arylalkenyloxycarbonyloxyalkyl such as 2-(3-phenylpropen-2-yloxycarbonyloxy)ethyl; alkoxycarbonylaminoalkyl such as t-butyloxycarbonylaminomethyl; alkylaminocarbonylaminoalkyl such as methylaminocarbonylaminomethyl; alkanoylaminoalkyl such as acetylaminomethyl; heterocycliccarbonyloxyalkyl such as 4-methylpiperazinylcarbonyloxymethyl; dialkylaminocarbonylalkyl such as dimethylaminocarbonylmethyl, diethylaminocarbonylmethyl; (5-(loweralkyl)-2-oxo-1,3-dioxolen4-yl)alkyl such as (5-t-butyl-2-oxo-1,3-dioxolen-4-yl)methyl; and (5-phenyl-2-oxo-1,3-dioxolen-4-yl)alkyl such as (5-phenyl-2-oxo-1,3-dioxolen-4-yl)methyl. Representative amide carboxy protecting groups comprise, without limitation, aminocarbonyl and loweralkylaminocarbonyl groups. Of the above carboxy-protecting groups, loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester are preferred. Preferred amide carboxy protecting groups are loweralkylaminocarbonyl groups.

In the solid phase peptide synthesis method, the α-C-terminal amino acid is attached to a suitable solid support or resin. Suitable solid supports useful for the above synthesis are those materials that are inert to the reagents and reaction conditions of the stepwise condensation-deprotection reactions, as well as being insoluble in the media used. The preferred solid support for synthesis of α-C-terminal carboxy peptides is 4-hydroxymethylphenoxymethyl-copoly (styrene-1% divinylbenzene). The preferred solid support for α-C-terminal amide peptides is the 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropyl-carbodiimide (DIC) or O-benzotriazol-1-yl-N,N,N',N'-tetramethyluronium-hexafluorophosphate (HBTU), with or without 4-dimethylaminopyridine (DMAP), 1-hydroxybenzotriazole (HOBT), benzotriazol-1-yloxy-tris(dimethylamino)phosphonium-hexafluorophosphate (BOP) or bis(2-oxo-3-oxazolidinyl)phosphine chloride (BOPCl), mediated coupling for from about 1 to about 24 hours at a temperature of between 10° C. and 50° C. in a solvent such as dichloromethane or DMF.

When the solid support is 4-(2',4'-dimethoxyphenyl-Fmoc-aminomethyl)-phenoxy-acetamidoethyl resin, the Fmoc group is cleaved with a secondary amine, preferably piperidine, prior to coupling with the α-C-terminal amino acid as described above. The preferred method for coupling to the deprotected 4-(2',4'-dimethoxyphenyl-Fmoc-aminomethyl)phenoxy-acetamidoethyl resin is O-benzotriazol-1-yl-N,N,N',N'-tetramethyluroniumhexafluoro-phosphate (HBTU, 1 equiv.), diisopropylethylamine (DIEA, 1 equiv.), and optionally 1-hydroxybenzotriazole (HOBT, 1 equiv.), in DMF. The coupling of successive protected amino acids can be carried out in an automatic polypeptide synthesizer in a conventional manner as is well known in the art.

The removal of the Fmoc protecting group from the α-N-terminal side of the growing peptide is accomplished conventionally, for example, by treatment with a secondary amine, preferably piperidine. Each protected amino acid is then introduced in about 3-fold molar excess, and the coupling is preferably carried out in DMF. The coupling agent is normally O-benzotriazol-1-yl-N,N,N',N'-tetramethyluroniumhexafluoro-phosphate (HBTU, 1 equiv.), diisopropylethylamine (DIEA, 1 equiv.), and optionally 1-hydroxybenzotriazole (HOBT, 1 equiv.).

At the end of the solid phase synthesis, the peptide is removed from the resin and deprotected, either in successive operations or in a single operation. Removal of the polypeptide and deprotection can be accomplished conventionally in a single operation by treating the resin-bound polypeptide with a cleavage reagent comprising thioanisole, triisopropylsilane, phenol, and trifluoroacetic acid. In cases wherein the α-C-terminal of the polypeptide is an alkylamide, the resin is cleaved by aminolysis with an alkylamine. Alternatively, the peptide may be removed by transesterification, e.g. with methanol, followed by aminolysis or by direct transamidation. The protected peptide may be purified at this point or taken to the next step directly. The removal of the side chain protecting groups is accomplished using the cleavage mixture described above. The fully deprotected peptide can be purified by a sequence of chromatographic steps employing any or all of the following types: ion exchange on a weakly basic resin (acetate form); hydrophobic adsorption chromatography on underivatized polystyrene-divinylbenzene (such as Amberlite XAD™); silica gel adsorption chromatography; ion exchange chromatography on carboxymethylcellulose; partition chromatography, e.g. on Sephadex G-25™, LH-20™ or countercurrent distribution; high performance liquid chromatography (HPLC), especially reverse-phase HPLC on octyl- or octadecylsilyl-silica bonded phase column packing. Anyone of ordinary skill in the art will be able to determine easily what would be the preferred chromatographic steps or sequences required to obtain acceptable purification of the GRF peptide.

Molecular weights of these peptides are determined using Quadrupole Electro Spray mass spectroscopy.

The synthesis process for the production of the GRF derivatives of the present invention will vary widely, depending upon the nature of the various elements, i.e., the GRF sequence, the linking group and the reactive entity, comprised in the GRF derivative. The synthetic procedures are selected to ensure simplicity, high yields and repetitivity, as well as to allow for a highly purified product. Normally, the chemically reactive group will be coupled at the last stage of the synthesis. Specific methods for the production of the present GRF derivatives are described below.

It is imperative that the chemically reactive entity be placed at a site to allow the peptide to bond to the blood component while retaining a substantial proportion, if not all, activity and/or beneficial effects of the original GRF peptide.

In a more preferred embodiment, each GRF derivative will be synthesized according to the following criteria: if a terminal carboxylic group is available on the peptide and is not critical for the retention of pharmacological activity, and no other sensitive functional group is present on the peptide, then the carboxylic acid will be chosen as attachment point for the linking group-reactive entity modification. If the terminal carboxylic group is involved in pharmacological activity, or if no carboxylic acids are available, then any other sensitive functional group not critical for the retention of pharmacological activity will be selected as the attachment point for the linking group-reactive entity modification. If several sensitive functional groups are available on a peptide, a combination of protecting groups will be used in such a way that after addition of the linking group/reactive entity and deprotection of all the protected sensitive functional groups, retention of pharmacological activity is still obtained. If no sensitive functional groups are available on the peptide, synthetic efforts will allow for a modification of the original peptide in such a way that retention of biological activity and retention of receptor or target specificity is obtained. In this case the modification should preferably occur at the opposite end of the peptide.

The present GRF derivatives may be used alone or in combination with other drugs or pharmaceutical products to optimize their therapeutic effects. They can be administered in a physiologically acceptable medium, e.g. deionized water, phosphate buffered saline (PBS), saline, aqueous ethanol or other alcohol, plasma, proteinaceous solutions, mannitol, aqueous glucose, alcohol, vegetable oil, or the like. Other additives which may be included include buffers, where the media are generally buffered at a pH in the range of about 5 to 10, where the buffer will generally range in concentration from about 50 to 250 mM, salt, where the concentration of salt will generally range from about 5 to 500 mM, physiologically acceptable stabilizers, and the like. The compositions may be lyophilized for convenient storage and transport.

The present peptide derivatives may be administered orally, parenterally, such as intravascularly (IV), intraarterially (IA), intramuscularly (IM), subcutaneously (SC), or the like. Administration may in appropriate situations be by transfusion. In some instances, where reaction of the functional group is relatively slow, administration may be oral, nasal, rectal, transdermal or aerosol, where the nature of the conjugate allows for transfer to the vascular system. Usually a single injection will be employed although more than one injection may be used, if desired. The peptide derivative may be administered by any convenient means, including syringe, trocar, catheter, or the like. The particular manner of administration will vary depending upon the amount to be administered, whether a single bolus or continuous administration, or the like. Preferably, the administration will be intravascularly, where the site of introduction is not critical to this invention, preferably at a site where there is rapid blood flow, e.g., intravenously, peripheral or central vein. Other routes may find use where the administration is coupled with slow release techniques or a protective matrix. The intent is that the peptides be effectively distributed in the blood, so as to be able to react with the blood components. The concentration of the conjugate will vary widely, generally ranging from about 1 pg/ml to 50 mg/ml. The total administered intravascularly will generally be in the range of about 0.1 mg/ml to about 10 mg/ml, more usually about 1 mg/ml to about 5 mg/ml.

By bonding to long-lived components of the blood, such as immunoglobulin, serum albumin, red blood cells and platelets, a number of advantages ensue. The activity of the present peptide derivatives is extended for days, and potentially up to weeks. Only one administration need be given during this period of time. Greater specificity can be achieved, since the active compound will be primarily bonded to large molecules, where it is less likely to be taken up intracellularly to interfere with other physiological processes.

The blood of the mammalian host may be monitored for the activity of the peptides and/or presence of the peptide derivatives. By taking a portion or sample of the blood of the host at different times, one may determine whether the peptide has become bonded to the long-lived blood components in sufficient amount to be therapeutically active and, thereafter, the level of peptide in the blood. If desired, one may also determine to which of the blood components the peptide is covalently bonded. For specific maleimide-substituted peptides, it simple to calculate the half-life of serum albumin and IgG. Monitoring may also take place by using assays of peptide activity, HPLC-MS or antibodies directed to peptides.

Another aspect of this invention relates to methods for determining the concentration of the GRF peptide or a conjugate thereof in biological samples (such as blood) using antibodies specific to the peptides and to the use of such antibodies as a treatment for toxicity potentially associated with such peptides or conjugates. This is advantageous because the extended presence and life of the GRF derivatives in vivo in the patient might lead to novel problems during treatment, including increased possibility for toxicity. The use of "anti-derivative" antibodies, either monoclonal or polyclonal, having specificity for particular derivatives, can assist in mediating any such problem. The antibody may be generated or derived from a host immunized with the particular modified peptide, or with an immunogenic fragment of the agent, or a synthesized immunogen corresponding to an antigenic determinant of the agent. Preferred antibodies will have high specificity and affinity for native, derivatized and conjugated forms of the peptide derivative. Such antibodies can also be labeled with enzymes, fluorochromes, or radiolables.

Antibodies specific for GRF derivatives may be produced by using purified peptides for the induction of derivatized peptide-specific antibodies. By induction of antibodies, it is intended not only the stimulation of an immune response by injection into animals, but analogous steps in the production of synthetic antibodies or other specific binding molecules such as screening of recombinant immunoglobulin libraries. Both monoclonal and polyclonal antibodies can be produced by procedures well known in the art.

The antibodies may also be used to monitor the presence of the derivative in the blood stream. Blood and/or serum samples may be analyzed by SDS-PAGE and western blotting. Such techniques permit the analysis of the blood or serum to determine the bonding of the GRF derivative to blood components.

The anti-therapeutic agent antibodies may also be used to treat toxicity induced by administration of the GRF derivative, and may be used ex vivo or in vivo. Ex vivo methods would include immuno-dialysis treatment for toxicity employing anti-therapeutic agent antibodies fixed to solid supports. In vivo methods include administration of anti-therapeutic agent antibodies in amounts effective to induce clearance of antibody-agent complexes.

The antibodies may be used to remove the GRF derivatives and conjugates thereof, from a patient's blood ex vivo by contacting the blood with the antibodies under sterile conditions. For example, the antibodies can be fixed or otherwise immobilized on a column matrix and the patient's blood can be removed from the patient and passed over the matrix. The GRF derivatives will bind to the antibodies and the blood containing a low concentration of the GRF derivative, then may be returned to the patient's circulatory system. The amount of GRF derivative removed can be controlled by adjusting the pressure and flow rate. Preferential removal of the GRF derivative from the plasma component of a patient's blood can be effected, for example, by the use of a semipermeable membrane, or by otherwise first separating the plasma component from the cellular component by ways known in the art prior to passing the plasma component over a matrix containing the anti-therapeutic antibodies. Alternatively the preferential removal of derivative-conjugated blood cells, including red blood cells, can be effected by collecting and concentrating the blood cells in the patient's blood and contacting those cells with fixed anti-peptide antibodies to the exclusion of the serum component of the patient's blood.

The anti-peptide antibodies can be administered in vivo, parenterally, to a patient that has received the GRF derivative or conjugates for treatment. The antibodies will bind the GRF derivative and conjugates. Once bound, the GRF derivative activity will be hindered if not completely blocked thereby reducing the biologically effective concentration of GRF derivative in the patient's bloodstream and minimizing harmful side effects. In addition, the bound antibody-peptide complex will facilitate clearance of the GRF derivative and conjugates from the patient's blood stream.

The following examples are provided to illustrate preferred embodiments of the invention, and shall by no means be construed as limiting the scope of thereof. Unless indicated otherwise, optically active protected amino acids in the L-configuration were used.

Synthesis

The synthesis of the GRF derivatives was performed using an automated solid-phase procedure on a Symphony™ peptide synthesizer with manual intervention during the generation of the derivatives. The synthesis was performed on Fmoc-protected Ramage™ amide linker resin, using Fmoc-protected amino acids. Coupling was achieved by using O-benzotriazol-1-yl-N,N,N',N'-tetramethyl-uronium hexafluorophosphate (HBTU) and diisopropylethylamine (DIEA) as the activator mixture in N,N-dimethylformamide (DMF) solution. The Fmoc protective group was removed using 20% piperidine/DMF. When needed, a Boc-protected amino acid was used at the N-terminus in order to generate the free N$_\alpha$-terminus after the peptide was cleaved from resin. All amino acids used during the synthesis possessed the L-sterochemistry unless otherwise stated. Sigmacoted glass reaction vessels were used during the synthesis.

EXAMPLE 1

Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-CONH$_2$

Step 1: Solid phase peptide synthesis was carried out on a 100 μmole scale. The following protected amino acids were sequentially added to resin: Fmoc-Arg(Pbf)—OH, Fmoc-Ser(tBu)—OH, Fmoc-Met-OH, Fmoc-Ile-OH, Fmoc-Asp(tBu)—OH, Fmoc-Gln(Trt)—OH, Fmoc-Leu-OH, Fmoc-Leu-OH, Fmoc-Lys(Boc)—OH, Fmoc-Arg(Pbf)—OH, Fmoc-Ala-OH, Fmoc-Ser(tBu)—OH, Fmoc-Leu-OH, Fmoc-Gln(Trt)—OH, Fmoc-Gly-OH, Fmoc-Leu-OH, Fmoc-Val-OH, Fmoc-Lys(Boc)—OH, Fmoc-Arg(Pbf)—OH, Fmoc-Tyr(tBu)—OH, Fmoc-Ser(tBu)—OH, Fmoc-Asn(Trt)—OH, Fmoc-Thr(tBu)—OH, Fmoc-Phe-OH, Fmoc-Ile-OH, Fmoc-Ala-OH, Fmoc-Asp(tBu)—OH, Fmoc-Ala-OH, Boc-Tyr(tBu)—OH. They were dissolved in N,N-dimethylformamide (DMF) and, according to the sequence, activated using O-benzotriazol-1-yl-N,N,N',N'-tetramethyl-uronium hexafluorophosphate (HBTU) and diisopropylethylamine (DIEA). Removal of the Fmoc protecting group was achieved using a solution of 20% (V/V) piperidine in N,N-dimethylformamide (DMF) for 20 minutes (step 1). The amino group of the final amino acid was acetylated using acetic acid activated using O-benzotriazol-1-yl-N,N,N',N'-tetramethyl-uronium hexafluorophosphate (HBTU) and diisopropylethylamine (DEA).

Step 2: The peptide was cleaved from the resin using 85% TFA/5% TIS/5% thioanisole and 5% phenol, followed by precipitation by dry-ice cold (0–4° C.) Et$_2$O. The crude peptide was collected on a polypropylene sintered funnel, dried, redissolved in a 40% mixture of acetonitrile in water (0.1% TFA) and lyophilized to generate the corresponding crude material used in the purification process.

EXAMPLE 2

Long Lasting Derivative of the GRF Peptide of Example 1

Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Lys(MPA)—CONH$_2$

Step 1: This step was performed as in Example 1 above, except that the first amino acid added to the resin was Fmoc-Lys(Aloc)—OH.

Step 2: The selective deprotection of the Lys (Aloc) group was performed manually and accomplished by treating the resin with a solution of 3 eq of Pd(PPh$_3$)$_4$ dissolved in 5 mL of C$_6$H$_6$:CHCl$_3$ (1:1): 2.5% NMM (v:v): 5% AcOH (v:v) for 2 h. The resin is then washed with CHCl$_3$ (6×5 mL), 20% AcOH in DCM (6×5 mL), DCM (6×5 mL), and DMF (6×5 mL).

Step 3: The synthesis was then re-automated for the addition of the 3-maleimidopropionic acid (MPA). Between every coupling, the resin was washed 3 times with N,N-dimethylformamide (DMF) and 3 times with isopropanol.

Step 4: The derivative was cleaved from the resin using 85% TFA/5% TIS/5% thioanisole and 5% phenol, followed by precipitation by dry-ice cold (0–4° C.) Et$_2$O. The crude derivative was collected on a polypropylene sintered funnel, dried, redissolved in a 40% mixture of acetonitrile in water (0.1% TFA) and lyophilized to generate the corresponding crude GRF derivative used in the purification process.

EXAMPLE 3

Tyr-(D)ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-CONH$_2$ (SEQ ID NO: 14)

Step 1: Solid phase peptide synthesis was carried out on a 100 μmole scale. The following protected amino acids were sequentially added to resin following the procedure described in step 1 of Example 1: Fmoc-Arg(Pbf)—OH, Fmoc-Ser(tBu)—OH, Fmoc-Met-OH, Fmoc-Ile-OH, Fmoc-Asp(tBu)—OH, Fmoc-Gln(Trt)—OH, Fmoc-Leu-OH, Fmoc-Leu-OH, Fmoc-Lys(Boc)—OH, Fmoc-Arg(Pbf)—OH, Fmoc-Ala-OH, Fmoc-Ser(tBu)—OH, Fmoc-Leu-OH, Fmoc-Gln(Trt)—OH, Fmoc-Gly-OH, Fmoc-Leu-OH, Fmoc-Val-OH, Fmoc-Lys(Boc)—OH, Fmoc-Arg(Pbf)—OH, Fmoc-Tyr(tBu)—OH, Fmoc-Ser(tBu)—OH, Fmoc-Asn(Trt)—OH, Fmoc-Thr(tBu)—OH, Fmoc-Phe-OH, Fmoc-Ile-OH, Fmoc-Ala-OH, Fmoc-Asp(tBu)—OH, Fmoc-(D)ala-OH, Boc-Tyr(tBu)—OH.

Step 2: This step was performed in the same manner as Step 2 of Example 1.

EXAMPLE 4

Long-Lasting Derivative of the GRF Peptide of Example 3

Tyr-(D)ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Lys(MPA)—CONH$_2$ (SEQ ID NO: 15)

Step 1: This step was performed as in Example 3, except that the first amino acid added to the resin was Fmoc-Lys (Aloc)—OH.

Steps 2–4: These steps were performed in the same manner as steps 2–4 of Example 2.

EXAMPLE 5

Tyr-(D)ala-Asp-Ala-Ile-Phe-Thr-Gln-Ser-Tyr-Arg-Lys-Val-Leu-Ala-Gln-Leu-Ser-Ala-Arg-Lys-Leu-Leu-Gln-Asp-Ile-Leu-Ser-Arg-CONH$_2$ (SEQ ID NO: 16)

Step 1: Solid phase peptide synthesis was carried out on a 100 μmole scale. The following protected amino acids were sequentially added to resin following the procedure described in step 1 of Example 1: Fmoc-Arg(Pbf)—OH, Fmoc-Ser(tBu)—OH, Fmoc-Leu-OH, Fmoc-Ile-OH, Fmoc-Asp(tBu)—OH, Fmoc-Gln(Trt)—OH, Fmoc-Leu-OH, Fmoc-Leu-OH, Fmoc-Lys(Boc)—OH, Fmoc-Arg(Pbf)—OH, Fmoc-Ala-OH, Fmoc-Ser(tBu)—OH, Fmoc-Leu-OH, Fmoc-Gln(Trt)—OH, Fmoc-Ala-OH, Fmoc-Leu-OH, Fmoc-Val-OH, Fmoc-Lys(Boc)—OH, Fmoc-Arg(Pbf)—OH, Fmoc-Tyr(tBu)—OH, Fmoc-Ser(tBu)—OH, Fmoc-Gln(Trt)—OH, Fmoc-Thr(tBu)—OH, Fmoc-Phe-OH, Fmoc-Ile-OH, Fmoc-Ala-OH, Fmoc-Asp(tBu)—OH, Fmoc-(D)ala-OH, Boc-Tyr(tBu)—OH.

Step 2: This step was performed in the same manner as Step 2 of Example 1.

EXAMPLE 6

Long-Lasting Derivative of the GRF Peptide of Example 5

Tyr-(D)ala-Asp-Ala-Ile-Phe-Thr-Gln-Ser-Tyr-Arg-Lys-Val-Leu-Ala-Gln-Leu-Ser-Ala-Arg-Lys-Leu-Leu-Gln-Asp-Ile-Leu-Ser-Arg-Lys(MPA)—CONH$_2$ (SEQ ID NO: 17)

Step 1: This step was performed as in Example 5, except that the first amino acid added to the resin was Fmoc-Lys(Aloc)—OH.

Steps 2–4: These steps were performed in the same manner as steps 2–4 of Example 2.

EXAMPLE 7

Tyr-(D)ala-Asp-Ala-Ile-Phe-Thr-Gln-Ser-Tyr-(D)Arg-Lys-Val-Leu-Ala-Gln-Leu-Ser-Ala-Arg-Lys-Leu-Leu-Gln-Asp-Ile-Leu-Ser-Arg-CONH$_2$ (SEQ ID NO: 18)

Step 1: Solid phase peptide synthesis was carried out on a 100 μmole scale. The following protected amino acids were sequentially added to resin following the procedure described in step 1 of Example 1: Fmoc-Arg(Pbf)—OH, Fmoc-Ser(tBu)—OH, Fmoc-Leu-OH, Fmoc-Ile-OH, Fmoc-Asp(tBu)—OH, Fmoc-Gln(Trt)—OH, Fmoc-Leu-OH, Fmoc-Leu-OH, Fmoc-Lys(Boc)—OH, Fmoc-Arg(Pbf)—OH, Fmoc-Ala-OH, Fmoc-Ser(tBu)—OH, Fmoc-Leu-OH, Fmoc-Gln(Trt)—OH, Fmoc-Ala-OH, Fmoc-Leu-OH, Fmoc-Val-OH, Fmoc-Lys(Boc)—OH, Fmoc-(D)Arg(Pbf)—OH, Fmoc-Tyr(tBu)—OH, Fmoc-Ser(tBu)—OH, Fmoc-Gln(Trt)—OH, Fmoc-Thr(tBu)—OH, Fmoc-Phe-OH, Fmoc-Ile-OH, Fmoc-Ala-OH, Fmoc-Asp(tBu)—OH, Fmoc-(D)Ala-OH, Boc-Tyr(tBu)—OH.

Step 2: This step was performed in the same manner as Step 2 of Example 1.

EXAMPLE 8

Long-Lasting Derivative of GRF Peptide of Example 7

Tyr-(D)Ala-Asp-Ala-Ile-Phe-Thr-Gln-Ser-Tyr-(D)Arg-Lys-Val-Leu-Ala-Gln-Leu-Ser-Ala-Arg-Lys-Leu-Leu-Gln-Asp-Ile-Leu-Ser-Arg-Lys(MPA)—CONH$_2$ (SEQ ID NO: 19)

Step 1: This step was performed as in Example 7, except that the first amino acid added to the resin was Fmoc-Lys(Aloc)—OH.

Steps 2–4: These steps were performed in the same manner as steps 2–4 of Example 2.

EXAMPLE 9

Tyr-(D)ala-Asp-Ala-Ile-Phe-Thr-Gln-Ser-Tyr-Arg-((N-Me)Lys)-Val-Leu-Ala-Gln-Leu-Ser-Ala-Arg-Lys-Leu-Leu-Gln-Asp-Ile-Leu-Ser-Arg-CONH$_2$ (SEQ ID NO: 20)

Step 1: Solid phase peptide synthesis was carried out on a 100 μmole scale. The following protected amino acids were sequentially added to resin following the procedure described in step 1 of Example 1: Fmoc-Arg(Pbf)—OH, Fmoc-Ser(tBu)—OH, Fmoc-Leu-OH, Fmoc-Ile-OH, Fmoc-Asp(tBu)—OH, Fmoc-Gln(Trt)—OH, Fmoc-Leu-OH, Fmoc-Leu-OH, Fmoc-Lys(Boc)—OH, Fmoc-Arg(Pbf)—OH, Fmoc-Ala-OH, Fmoc-Ser(tBu)—OH, Fmoc-Leu-OH, Fmoc-Gln(Trt)—OH, Fmoc-Ala-OH, Fmoc-Leu-OH, Fmoc-Val-OH, Fmoc-(N-Me)Lys(Boc)—OH, Fmoc-Arg(Pbf)—OH, Fmoc-Tyr(tBu)—OH, Fmoc-Ser(tBu)—OH, Fmoc-Gln(Trt)—OH, Fmoc-Thr(tBu)—OH, Fmoc-Phe-OH, Fmoc-Ile-OH, Fmoc-Ala-OH, Fmoc-Asp(tBu)—OH, Fmoc-(D)Ala-OH, Boc-Tyr(tBu)—OH.

Step 2: This step was performed in the same manner as Step 2 of Example 1.

EXAMPLE 10

Long-Lasting Derivative of the GRF Peptide of Example 9

Tyr-(D)ala-Asp-Ala-Ile-Phe-Thr-Gln-Ser-Tyr-Arg-((N-Me)Lys)-Val-Leu-Ala-Gln-Leu-Ser-Ala-Arg-Lys-Leu-Leu-Gln-Asp-Ile-Leu-Ser-Arg-Lys(MPA)—CONH$_2$ (SEQ ID NO: 21)

Step 1: This step was performed as in Example 9, except that the first amino acid added to the resin was Fmoc-Lys(Aloc)—OH.

Steps 2–4: These steps were performed in the same manner as steps 2–4 of Example 2.

EXAMPLE 11

Second Long Lasting Derivative of the GRF Peptide of Example 9

Tyr-(D)ala-Asp-Ala-Ile-Phe-Thr-Gln-Ser-Tyr-Arg-Lys(MPA)-Val-Leu-Ala-Gln-Leu-Ser-Ala-Arg-Lys-Leu-Leu-Gln-Asp-Ile-Leu-Ser-Arg-CONH$_2$ (SEQ ID NO: 22)

Step 1: Solid phase peptide synthesis was carried out on a 100 μmole scale. The following protected amino acids were sequentially added to resin following the procedure described in step 1 of Example 1: Fmoc-Arg(Pbf)—OH, Fmoc-Ser(tBu)—OH, Fmoc-Leu-OH, Fmoc-Ile-OH, Fmoc-Asp(tBu)—OH, Fmoc-Gln(Trt)—OH, Fmoc-Leu-OH, Fmoc-Leu-OH, Fmoc-Lys(Boc)—OH, Fmoc-Arg(Pbf)—OH, Fmoc-Ala-OH, Fmoc-Ser(tBu)—OH, Fmoc-Leu-OH, Fmoc-Gln(Trt)—OH, Fmoc-Ala-OH, Fmoc-Leu-OH, Fmoc-Val-OH, Fmoc-Lys(Aloc)—OH, Fmoc-Arg(Pbf)—OH, Fmoc-Tyr(tBu)—OH, Fmoc-Ser(tBu)—OH, Fmoc-Gln(Trt)—OH, Fmoc-Thr(tBu)—OH, Fmoc-Phe-OH, Fmoc-Ile-OH, Fmoc-Ala-OH, Fmoc-Asp(tBu)—OH, Fmoc-(D)Ala-OH, Boc-Tyr(tBu)—OH.

Steps 2–4: These steps were performed in the same manner as steps 2–4 of Example 2.

EXAMPLE 12

Beef GRF

Tyr-(D)ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Asn-Arg-CONH$_2$ (SEQ ID NO: 23)

Step 1: Solid phase peptide synthesis was carried out on a 100 μmole scale. The following protected amino acids were sequentially added to resin following the procedure described in step 1 of Example 1: Fmoc-Arg(Pbf)—OH, Fmoc-Asn(Trt)—OH, Fmoc-Met-OH, Fmoc-Ile-OH, Fmoc-Asp(tBu)—OH, Fmoc-Gln(Trt)—OH, Fmoc-Leu-OH, Fmoc-Leu-OH, Fmoc-Lys(Boc)—OH, Fmoc-Arg(Pbf)—OH, Fmoc-Ala-OH, Fmoc-Ser(tBu)—OH, Fmoc-Leu-OH, Fmoc-Gln(Trt)—OH, Fmoc-Gly-OH, Fmoc-Leu-OH, Fmoc-Val-OH, Fmoc-Lys(Boc)—OH, Fmoc-Arg(Pbf)—OH, Fmoc-Tyr(tBu)—OH, Fmoc-Ser(tBu)—OH, Fmoc-Asn(Trt)—OH, Fmoc-Thr(tBu)—OH, Fmoc-Phe-OH, Fmoc-Ile-OH, Fmoc-Ala-OH, Fmoc-Asp(tBu)—OH, Fmoc-(D)ala-OH, Boc-Tyr(tBu)—OH.

Step 2: This step was performed in the same manner as Step 2 of Example 1.

EXAMPLE 13

Long Lasting Derivative of the GRF Peptide of Example 12

Tyr-(D)ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Asn-Lys(MPA)—CONH$_2$ (SEQ ID NO: 24)

Step 1: This step was performed as in Example 12, except that the first amino acid added to the resin was Fmoc-Lys (Aloc)—OH.

Steps 2–4: These steps were performed in the same manner as steps 2–4 of Example 2.

EXAMPLE 14

Beef GRF

Tyr-(D)ala-Asp-Ala-Ile-Phe-Thr-Gln-Ser-Tyr-Arg-Lys-Val-Leu-Ala-Gln-Leu-Ser-Ala-Arg-Lys-Leu-Leu-Gln-Asp-Ile-Leu-Asn-Arg-CONH$_2$ (SEQ ID NO: 25)

Step 1: Solid phase peptide synthesis was carried out on a 100 μmole scale. The following protected amino acids were sequentially added to resin following the procedure described in step 1 of Example 1: Fmoc-Arg(Pbf)—OH, Fmoc-Asn(Trt)—OH, Fmoc-Leu-OH, Fmoc-Ile-OH, Fmoc-Asp(tBu)—OH, Fmoc-Gln(Trt)—OH, Fmoc-Leu-OH, Fmoc-Leu-OH, Fmoc-Lys(Boc)—OH, Fmoc-Arg(Pbf)—OH, Fmoc-Ala-OH, Fmoc-Ser(tBu)—OH, Fmoc-Leu-OH, Fmoc-Gln(Trt)—OH, Fmoc-Ala-OH, Fmoc-Leu-OH, Fmoc-Val-OH, Fmoc-Lys(Boc)—OH, Fmoc-Arg(Pbf)—OH, Fmoc-Tyr(tBu)—OH, Fmoc-Ser(tBu)—OH, Fmoc-Gln(Trt)—OH, Fmoc-Thr(tBu)—OH, Fmoc-Phe-OH, Fmoc-Ile-OH, Fmoc-Ala-OH, Fmoc-Asp(tBu)—OH, Fmoc-(D)ala-OH, Boc-Tyr(tBu)—OH.

Step 2: This step was performed in the same manner as Step 2 of Example 1.

EXAMPLE 14

Long Lasting Derivative of the GRF Peptide of Example 13

Tyr-(D)ala-Asp-Ala-Ile-Phe-Thr-Gln-Ser-Tyr-Arg-Lys-Val-Leu-Ala-Gln-Leu-Ser-Ala-Arg-Lys-Leu-Leu-Gln-Asp-Ile-Leu-Asn-Arg-Lys(AEEA-MPA)—CONH$_2$ (SEQ ID NO: 26)

Step 1: This step was performed as in Example 13, except that the first amino acid added to the resin was Fmoc-Lys (Aloc)—OH.

Step 2: The selective deprotection of the Lys (Aloc) group was performed manually and accomplished by treating the resin with a solution of 3 eq of Pd(PPh$_3$)$_4$ dissolved in 5 mL of C$_6$H$_6$:CHCl$_3$ (1:1):2.5% NMM (v:v):5% AcOH (v:v) for 2 h (Step 2). The resin is then washed with CHCl$_3$ (6×5 mL), 20% AcOH in DCM (6×5 mL), DCM (6×5 mL), and DMF (6×5 mL).

Step 3: The synthesis was then re-automated for the addition of the Fmoc-AEEA-OH (Fmoc-aminoethoxyethoxy acetic acid). Between every coupling, the resin was washed 3 times with N,N-dimethylformamide (DMF) and 3 times with isopropanol. After proper deprotection, MPA (3-maleimidopropionic acid) was anchored to the AEEA spacer and again the resin was washed 3 times with N,N-dimethylformamide (DMF) and 3 times with isopropanol.

Step 4: The peptide was cleaved from the resin using 85% TFA/5% TIS/5% thioanisole and 5% phenol, followed by precipitation by dry-ice cold Et$_2$O (0–4° C.). The crude derivative was collected on a polypropylene sintered funnel, dried, redissolved in a 40% mixture of acetonitrile in water (0.1% TFA) and lyophilized to generate the corresponding crude derivative used in the purification process.

EXAMPLE 15

Beef GRF

Tyr-(D)ala-Asp-Ala-Ile-Phe-Thr-Gln-Ser-Tyr-(D)arg-Lys-Val-Leu-Ala-Gln-Leu-Ser-Ala-Arg-Lys-Leu-Leu-Gln-Asp-Ile-Leu-Asn-Arg-CONH$_2$ (SEQ ID NO: 27)

Step 1: Solid phase peptide synthesis was carried out on a 100 μmole scale. The following protected amino acids were sequentially added to resin following the procedure described in step 1 of Example 1: Fmoc-Arg(Pbf)—OH, Fmoc-Asn(Trt)—OH, Fmoc-Leu-OH, Fmoc-Ile-OH, Fmoc-Asp(tBu)—OH, Fmoc-Gln(Trt)—OH, Fmoc-Leu-OH, Fmoc-Leu-OH, Fmoc-Lys(Boc)—OH, Fmoc-Arg(Pbf)—OH, Fmoc-Ala-OH, Fmoc-Ser(tBu)—OH, Fmoc-Leu-OH, Fmoc-Gln(Trt)—OH, Fmoc-Ala-OH, Fmoc-Leu-OH, Fmoc-Val-OH, Fmoc-Lys(Boc)—OH, Fmoc-(D)arg(Pbf)—OH, Fmoc-Tyr(tBu)—OH, Fmoc-Ser(tBu)—OH, Fmoc-Gln(Trt)—OH, Fmoc-Thr(tBu)—OH, Fmoc-Phe-OH, Fmoc-Ile-OH, Fmoc-Ala-OH, Fmoc-Asp(tBu)—OH, Fmoc-(D)ala-OH, Boc-Tyr(tBu)—OH.

Step 2: This step was performed in the same manner as Step 2 of Example 1.

EXAMPLE 16

Long Lasting Derivative of the GRF Peptide of Example 15

Tyr-(D)ala-Asp-Ala-Ile-Phe-Thr-Gln-Ser-Tyr-(D)arg-Lys-Val-Leu-Ala-Gln-Leu-Ser-Ala-Arg-Lys-Leu-Leu-Gln-Asp-Ile-Leu-Asn-Arg-Lys(AEEA-MPA)—CONH$_2$ (SEQ ID NO: 28)

Step 1: This step was performed as in Example 15, except that the first amino acid added to the resin was Fmoc-Lys (Aloc)—OH.

Steps 2–4: These steps were performed in the same manner as steps 2–4 of Example 14.

EXAMPLE 17

Beef GRF

Tyr-(D)ala-Asp-Ala-Ile-Phe-Thr-Gln-Ser-Tyr-Arg-((N-Me)Lys)-Val-Leu-Ala-Gln-Leu-Ser-Ala-Arg-Lys-Leu-Leu-Gln-Asp-Ile-Leu-Asn-Arg-CONH$_2$ (SEQ ID NO: 29)

Step 1: Solid phase peptide synthesis was carried out on a 100 μmole scale. The following protected amino acids were sequentially added to resin following the procedure described in step 1 of Example 1: Fmoc-Arg(Pbf)—OH, Fmoc-Asn(Trt)—OH, Fmoc-Leu-OH, Fmoc-Ile-OH, Fmoc-Asp(tBu)—OH, Fmoc-Gln(Trt)—OH, Fmoc-Leu-OH, Fmoc-Leu-OH, Fmoc-Lys(Boc)—OH, Fmoc-Arg(Pbf)—OH, Fmoc-Ala-OH, Fmoc-Ser(tBu)—OH, Fmoc-Leu-OH, Fmoc-Gln(Trt)—OH, Fmoc-Ala-OH, Fmoc-Leu-OH, Fmoc-Val-OH, Fmoc-(N-Me)Lys(Boc)—OH, Fmoc-Arg(Pbf)—OH, Fmoc-Tyr(tBu)—OH, Fmoc-Ser(tBu)—OH, Fmoc-Gln(Trt)—OH, Fmoc-Thr(tBu)—OH, Fmoc-Phe-OH, Fmoc-Ile-OH, Fmoc-Ala-OH, Fmoc-Asp(tBu)—OH, Fmoc-(D)ala-OH, Boc-Tyr(tBu)—OH.

Step 2: This step was performed in the same manner as Step 2 of Example 1.

EXAMPLE 18

Long Lasting Derivative of the GRF Peptide of Example 17

Tyr-(D)ala-Asp-Ala-Ile-Phe-Thr-Gln-Ser-Tyr-Arg-((N-Me)Lys)Val-Leu-Ala-Gln-Leu-Ser-Ala-Arg-Lys-Leu-Leu-Gln-Asp-Ile-Leu-Asn-Arg-Lys(MPA)—CONH$_2$ (SEQ ID NO: 30)

Step 1: This step was performed as in Example 17, except that the first amino acid added to the resin was Fmoc-Lys(Aloc)—OH.

Steps 2–4: These steps were performed in the same manner as steps 2–4 of Example 2.

EXAMPLE 19

Second Long Lasting Derivative of the GRF Peptide of Example 17

Tyr-(D)ala-Asp-Ala-Ile-Phe-Thr-Gln-Ser-Tyr-Arg-Lys(MPA)-Val-Leu-Ala-Gln-Leu-Ser-Ala-Arg-Lys-Leu-Leu-Gln-Asp-Ile-Leu-Asn-Arg-CONH$_2$ (SEQ ID NO: 31)

Step 1: Solid phase peptide synthesis was carried out on a 100 µmole scale. The following protected amino acids were sequentially added to resin following the procedure described in step 1 of Example 1: Fmoc-Arg(Pbf)—OH, Fmoc-Asn(Trt)—OH, Fmoc-Leu-OH, Fmoc-Ile-OH, Fmoc-Asp(tBu)—OH, Fmoc-Gln(Trt)—OH, Fmoc-Leu-OH, Fmoc-Leu-OH, Fmoc-Lys(Boc)—OH, Fmoc-Arg(Pbf)—OH, Fmoc-Ala-OH, Fmoc-Ser(tBu)—OH, Fmoc-Leu-OH, Fmoc-Gln(Trt)—OH, Fmoc-Ala-OH, Fmoc-Leu-OH, Fmoc-Val-OH, Fmoc-Lys(Aloc)—OH, Fmoc-Arg(Pbf)—OH, Fmoc-Tyr(tBu)—OH, Fmoc-Ser(tBu)—OH, Fmoc-Gln(Trt)—OH, Fmoc-Thr(tBu)—OH, Fmoc-Phe-OH, Fmoc-Ile-OH, Fmoc-Ala-OH, Fmoc-Asp(tBu)—OH, Fmoc-(D)ala-OH, Boc-Tyr(tBu)—OH.

Steps 2–4: These steps were performed in the same manner as steps 2–4 of Example 2.

EXAMPLE 20

Salmon GRF

His-(D)ala-Asp-Gly-Met-Phe-Asn-Lys-Ala-Tyr-Arg-Lys-(MPA)-Ala-Leu-Gly-Gln-Leu-Ser-Ala-Arg-Lys-Tyr-Leu-His-Ser-Leu-Met-Ala-Lys-CONH$_2$ (SEQ ID NO: 32)

Step 1: Solid phase peptide synthesis was carried out on a 100 µmole scale. The following protected amino acids were sequentially added to resin following the procedure described in step 1 of Example 1: Fmoc-Lys(Boc)—OH, Fmoc-Ala-OH, Fmoc-Met-OH, Fmoc-Leu-OH, Fmoc-Ser(tBu)—OH, Fmoc-His(Trt)—OH, Fmoc-Leu-OH, Fmoc-Tyr(tBu)—OH, Fmoc-Lys(Boc)—OH, Fmoc-Arg(Pbf)—OH, Fmoc-Ala-OH, Fmoc-Ser(tBu)—OH, Fmoc-Leu-OH, Fmoc-Gln(Trt)—OH, Fmoc-Gly-OH, Fmoc-Leu-OH, Fmoc-Ala-OH, Fmoc-Lys(Boc)—OH, Fmoc-Arg(Pbf)—OH, Fmoc-Tyr(tBu)—OH, Fmoc-Ala-OH, Fmoc-Lys(Boc)—OH, Fmoc-Asn(Trt)—OH, Fmoc-Phe-OH, Fmoc-Met-OH, Fmoc-Gly-OH, Fmoc-Asp(tBu)—OH, Fmoc-(D)ala-OH, Boc-His(Boc)—OH.

Step 2: This step was performed in the same manner as Step 2 of Example 1.

EXAMPLE 21

Long Lasting Derivative of the GRF Peptide of Example 20

His-(D)ala-Asp-Gly-Met-Phe-Asn-Lys-Ala-Tyr-Arg-Lys-Ala-Leu-Gly-Gln-Leu-Ser-Ala-Arg-Lys-Tyr-Leu-His-Ser-Leu-Met-Ala-Lys(AEEA-MPA)—CONH$_2$ (SEQ ID NO: 33)

Step 1: This step was performed as in Example 20.

Steps 2–4: These steps were performed in the same manner as steps 2–4 of Example 14.

EXAMPLE 22

Salmon GRF

Second Long Lasting Derivative of the GRF Peptide of Example 20

His-(D)ala-Asp-Gly-Met-Phe-Asn-Lys-Ala-Tyr-Arg-Lys(MPA)-Ala-Leu-Gly-Gln-Leu-Ser-Ala-Arg-Lys-Tyr-Leu-His-Ser-Leu-Met-Ala-Lys-CONH$_2$ (SEQ ID NO: 34)

Step 1: Solid phase peptide synthesis was carried out on a 100 µmole scale. The following protected amino acids were sequentially added to resin following the procedure described in step 1 of Example 1: Fmoc-Lys(Boc)—OH, Fmoc-Ala-OH, Fmoc-Met-OH, Fmoc-Leu-OH, Fmoc-Ser(tBu)—OH, Fmoc-His(Trt)OH, Fmoc-Leu-OH, Fmoc-Tyr(tBu)—OH, Fmoc-Lys(Boc)—OH, Fmoc-Arg(Pbf)—OH, Fmoc-Ala-OH, Fmoc-Ser(tBu)—OH, Fmoc-Leu-OH, Fmoc-Gln(Trt)—OH, Fmoc-Gly-OH, Fmoc-Leu-OH, Fmoc-Ala-OH, Fmoc-Lys(Aloc)—OH, Fmoc-Arg(Pbf)—OH, Fmoc-Tyr(tBu)—OH, Fmoc-Ala-OH, Fmoc-Lys(Boc)—OH, Fmoc-Asn(Trt)—OH, Fmoc-Phe-OH, Fmoc-Met-OH, Fmoc-Gly-OH, Fmoc-Asp(tBu)—OH, Fmoc-(D)ala-OH, Boc-His(Boc)—OH.

Steps 2–4: These steps were performed in the same manner as steps 2–4 of Example 2.

EXAMPLE 23

Chicken GRF

His-(D)ala-Asp-Gly-Ile-Phe-Ser-Lys-Ala-Tyr-Arg-Lys-Leu-Leu-Gly-Gln-Leu-Ser-Ala-Arg-Asn-Tyr-Leu-His-Ser-Leu-Met-Ala-Lys-CONH$_2$ (SEQ ID NO: 35)

Step 1: Solid phase peptide synthesis was carried out on a 100 µmole scale. The following protected amino acids were sequentially added to resin following the procedure described in step 1 of Example 1: Fmoc-Lys(Boc)—OH, Fmoc-Ala-OH, Fmoc-Met-OH, Fmoc-Leu-OH, Fmoc-Ser(tBu)—OH, Fmoc-His(Trt)—OH, Fmoc-Leu-OH, Fmoc-Tyr(tBu)—OH, Fmoc-Asn(Trt)—OH, Fmoc-Arg(Pbf)—OH, Fmoc-Ala-OH, Fmoc-Ser(tBu)—OH, Fmoc-Leu-OH, Fmoc-Gln(Trt)—OH, Fmoc-Gly-OH, Fmoc-Leu-OH, Fmoc-Leu-OH, Fmoc-Lys(Boc)—OH, Fmoc-Arg(Pbf)—OH, Fmoc-Tyr(tBu)—OH, Fmoc-Ala-OH, Fmoc-Lys(Boc)—OH, Fmoc-Ser(tBu)—OH, Fmoc-Phe-OH, Fmoc-Ile-OH, Fmoc-Gly-OH, Fmoc-Asp(tBu)—OH, Fmoc-(D)ala-OH, Boc-His(Boc)—OH.

Step 2: This step was performed in the same manner as Step 2 of Example 1.

EXAMPLE 24

Long Lasting Derivative of the GRF Peptide of Example 23

His-(D)ala-Asp-Gly-Ile-Phe-Ser-Lys-Ala-Tyr-Arg-Lys-Leu-Leu-Gly-Gln-Leu-Ser-Ala-Arg-Asn-Tyr-Leu-His-Ser-Leu-Met-Ala-Lys(AEEA-MPA)—CONH$_2$ (SEQ ID NO: 36)

Step 1: This step was performed as in Example 23.

Steps 2–4: These steps were performed in the same manner as steps 2–4 of Example 14.

EXAMPLE 25

Second Long Lasting Derivative of the GRF Peptide of Example 23

His-(D)ala-Asp-Gly-Ile-Phe-Ser-Lys-Ala-Tyr-Arg-Lys (MPA)-Leu-Leu-Gly-Gln-Leu-Ser-Ala-Arg-Asn-Tyr-Leu-His-Ser-Leu-Met-Ala-Lys-CONH$_2$ (SEQ ID NO: 37)

Step 1: Solid phase peptide synthesis was carried out on a 100 µmole scale. The following protected amino acids were sequentially added to resin following the procedure described in step 1 of Example 1: Fmoc-Lys(Boc)—OH, Fmoc-Ala-OH, Fmoc-Met-OH, Fmoc-Leu-OH, Fmoc-Ser(tBu)—OH, Fmoc-His(Trt)—OH, Fmoc-Leu-OH, Fmoc-Tyr(tBu)—OH, Fmoc-Asn(Trt)—OH, Fmoc-Arg(Pbf)—OH, Fmoc-Ala-OH, Fmoc-Ser(tBu)—OH, Fmoc-Leu-OH, Fmoc-Gln(Trt)—OH, Fmoc-Gly-OH, Fmoc-Leu-OH, Fmoc-Leu-OH, Fmoc-Lys(Aloc)—OH, Fmoc-Arg(Pbf)—OH, Fmoc-Tyr(tBu)—OH, Fmoc-Ala-OH, Fmoc-Lys(Boc)—OH, Fmoc-Ser(tBu)—OH, Fmoc-Phe-OH, Fmoc-Ile-OH, Fmoc-Gly-OH, Fmoc-Asp(tBu)—OH, Fmoc-(D)ala-OH, Boc-His(Boc)—OH.

Steps 2–4: These steps were performed in the same manner as steps 2–4 of Example 2.

EXAMPLE 26

Second Long Lasting Derivative of the GRF Peptide of Example 1

(N-MPA)-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-CONH$_2$

Step 1: This step was performed as in Example 1 above, except that the last component (MPA) is added to the resin at the end of the synthesis.

Step 2: The derivative was cleaved from the resin using 85% TFA/5% TIS/5% thioanisole and 5% phenol, followed by precipitation by dry-ice cold (0–4° C.) Et$_2$O. The crude derivative was collected on a polypropylene sintered funnel, dried, redissolved in a 40% mixture of acetonitrile in water (0.1% TFA) and lyophilized to generate the corresponding crude GRF derivative used in the purification process.

EXAMPLE 27

Third Long Lasting Derivative of the GRF Peptide of Example 1

(N-AEEA-MPA)-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-CONH$_2$

Step 1: This step was performed as in Example 1 above, except that the second last component is Fmoc-AEEA, and the last component is (MPA).

Step 2: This step is the same as step 2 of Example 26.

Purification Procedure:

Each compound was purified by preparative reversed phase HPLC, using a Varian (Dynamax) preparative binary HPLC system. The purification was performed using a Phenomenex Luna 10µ phenyl-hexyl, 50 mm×250 mm column (particles 10µ) equilibrated with a water/TFA mixture (0.1% TFA in H$_2$O (solvent A) and acetonitrile/TFA (0.1% TFA in CH$_3$CN (solvent B). Elution was achieved at 50 mL/min by running a 28–38% B gradient over 180 min. Fractions containing peptide were detected by UV absorbance (Varian Dynamax UVD II) at 214 and 254 nm.

The fractions were collected in 25 mL aliquots. Those containing the desired product were identified by mass detection after direct injection onto LC/MS. The selected fractions were subsequently analyzed by analytical HPLC (20–60% B over 20 min; Phenomenex Luna 5 µ phenyl-bexyl, 10 mm×250 mm column, 0.5 mL/min) to identify fractions with ≧90% purity for pooling. The pool was freeze-dried using liquid nitrogen and subsequently lyophilized for at least 2 days to yield a white powder.

In vitro Results

The potency of some of the present GRF derivatives was assessed as their ability to significantly increase GH secretion in a rat primary anterior pituitary cell culture assay. Fresh rat primary pituitary cells were exposed to various concentrations of the compounds for four hours and GH levels in the culture media were determined using a commercially available RIA kit from Linco Research (MO).

Methodology

Whole pituitaries were removed from anesthetized normal Sprague-Dawley rats and directly collected into fresh culture media containing fungizone and gentamicin sulfate. Cells were prepared for primary cell culture within one-hour post-pituitary collection. Individual pituitaries were minced and tissue fragments were digested with trypsin with continuous gentle agitation. Tissues pieces were mechanically disrupted using a Pasteur pipette and incubated for an additional 15 minutes. Cells were triturated, washed twice and seeded in 24 well-plates containing fresh media. After 72 hours of culture, cells were washed twice with serum-free media and then incubated with or without a GRF analog or derivative for four hours. After incubation, supernatants were collected and assayed for quantitative determination of rat growth hormone by radioimmunoassay (kit from Linco Research, (MO).

As it can be seen in the Figures, the results show that all the present GRF derivatives were able to stimulate GH secretion at concentrations ranging between $10^{-6}$ to $10^{-13}$ M. The index of stimulation was comparable to that obtained with commercial GRF(1–29) and D-Ala-GRF(1–29) (both from Polypeptide Laboratories, California).

In vivo Results

The in vivo potency of the present GRF derivatives was assessed as their ability to significantly increase GH secretion in freely moving animals. The compounds were administered subcutaneously as bolus injection (1 µmol/kg) to catheterized normal Sprague-Dawley rats. Serial blood samples were taken to measure acute GH release following compound administration.

Methodology

Catheterized 7–8 week-old male Sprague-Dawley rats were fitted with a rat harness at least 5 days prior to experimentation to avoid stress. Experimentation onset was only between 9 AM and 11 AM. Each treatment group consisted of 8 rats. The compounds were administered once by a subcutaneous injection in the dorso-lombar area. Serial blood samples were taken pre-dose, and at 5, 10, 15, 20, 30 and 60 minutes post-injection. Plasma were harvested and samples sent directly to Linco Research (MO) for GH determination by radioimmunoassay. Statistical determinations (t-TEST) were performed using MicroSoft ExCel™ software.

As in can be seen in the Figures, all the present GRF derivatives were able to induce GH secretion in a normal rat model.

Pharmacokinetic Studies

Figure 9:
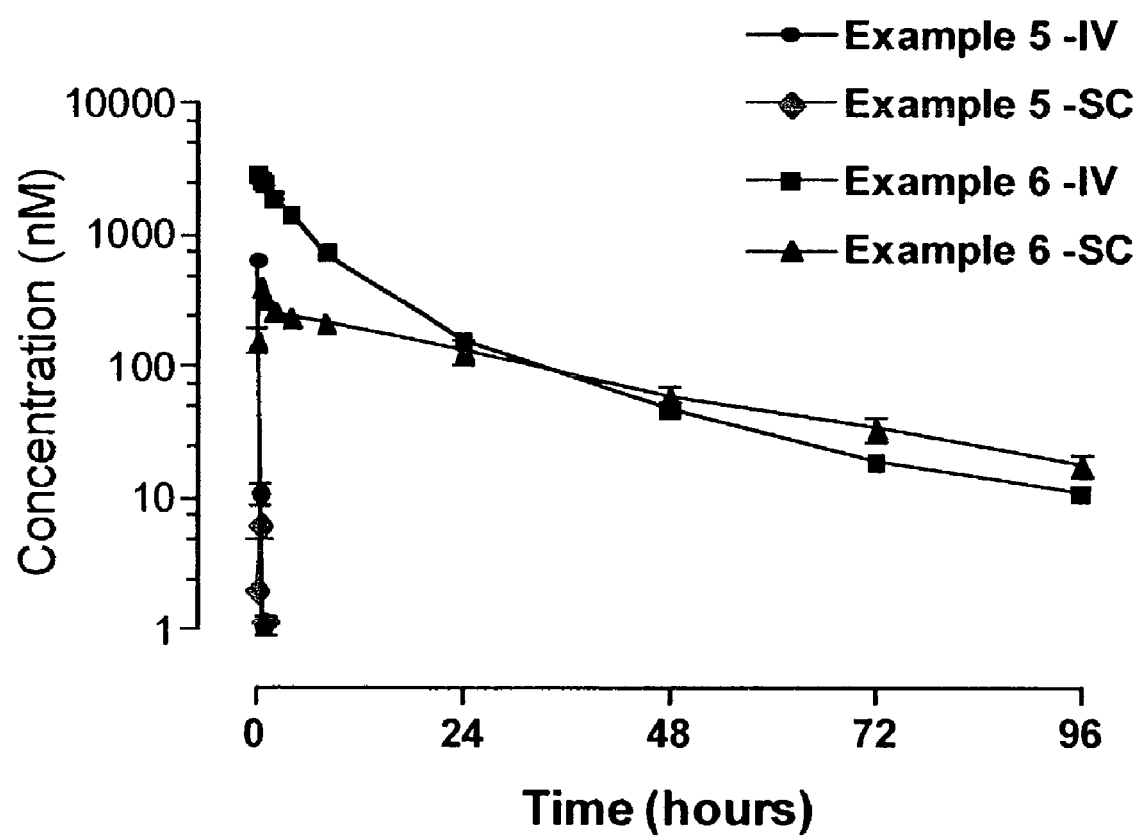
FIG. 9 illustrates the pharmacokinetic profiles of the compounds of Examples 5 and 6 in male Sprague-Dawley rats.

Pharmacokinetic studies were carried out on the compounds of Examples 5 and 6. Each compound was injected subcutaneously (1 μmol/kg) or intravenously (100 nmol/kg) to male Sprague-Dawley rats. Serial blood samples were taken at pre-dose, 5, 30 and 60 minutes and 2, 4, 8, 24, 48, 72 and 96 hours post-agent administration. Plasma were harvested and frozen until analysis by radioimmunoassay (RIA). A commercial polyclonal antibody raised against human native GRF (1–29) was used to detect the compounds. The assay sensitivity was 300 to 10 000 pM. Consequently, some samples had to be diluted for analysis. The results of the pharmacokinetic profiles appear in FIG. 9. As it can be seen, the compound of Example 5, i.e., the native peptide, disappears very rapidly. In fact, the compound of Example 5, whether administered subcutaneously or intrasvenously, could not be detected after 60 minutes post administration. This is consistent with results in Sprague-Dawley rats reported in the literature for GRF (1–29) and other analogues thereof, regarding the terminal half-life thereof and the percentage of bioavailability (SC/IV) (see for example *Peptides,* 9:207–209, and *J. Endocr.,* 107: R5–R8.

On the other hand, the compound of Example 6, which is the native peptide of Example 5 derivatized in accordance with the present invention, remains detectable after 96 hours. Additional data is present in the Table 2 below.

TABLE 2

Pharmacokinetic parameters for the compound of Example 6

| Parameters | Subcutaneous administration | Intravenous administration |
| --- | --- | --- |
| λ | 0.027 | 0.037 |
| Terminal half-life (hours) | 25.8 ± 2.1 | 18.7 ± 1.4 |
| AUC (nM × h) | 8864.5 | 23277.5 |
| % bioavailability (SC/IV) | 3.8 | N/A |

While the invention has been described in connection with specific embodiments thereof, it will be understood that it is capable of further modifications, and this application is intended to cover any variations, uses or adaptations of the invention following, in general, the principles of the invention, and including such departures from the present description as come within known or customary practice within the art to which the invention pertains, and as may be applied to the essential features hereinbefore set forth, and as follows in the scope of the appended claims.

What is claimed is:

1. A growth hormone releasing factor derivative comprising:

Tyr-(D)ala-Asp-Ala-Ile-Phe-Thr-Gln-Ser-Tyr-Arg-Lys-Val-Leu-Ala-Gln-Leu-Ser-Ala-Arg-Lys-Leu-Leu-Gln-Asp-Ile-Leu-Ser-Arg-Lys(MPA)—CONH$_2$ (SEQ ID NO: 6).

2. A conjugate of the following formula:

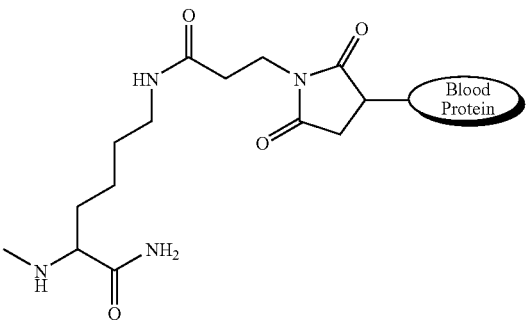

Tyr-(D)ala-Asp-Ala-Ile-Phe-Thr-Gln-Ser-Tyr-Arg-Lys-Val-Leu-Ala-Gln-Leu-Ser-Ala-Arg-Lys-Leu-Leu-Gln-Asp-Ile-Leu-Ser-Arg 3. A conjugate of the following formula:

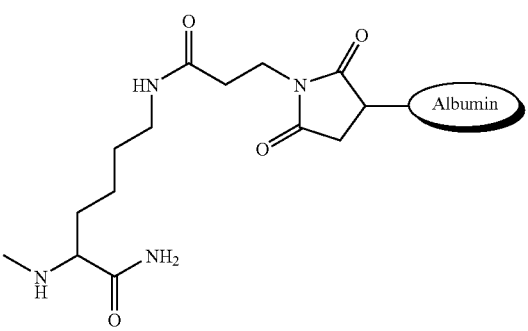

Tyr-(D)ala-Asp-Ala-Ile-Phe-Thr-Gln-Ser-Tyr-Arg-Lys-Val-Leu-Ala-Gln-Leu-Ser-Ala-Arg-Lys-Leu-Leu-Gln-Asp-Ile-Leu-Ser-Arg 4. A pharmaceutical composition comprising the derivative of claim 1 in combination with a pharmaceutical carrier.

5. The composition of claim 4 for the promotion of endogenous growth hormone production or release in a subject.

6. The composition of claim 4 treating diseases or conditions resulting from growth hormone production abnormalities.

7. A method for treating a disease or condition resulting from a growth hormone production abnormality in a subject, comprising administering to the subject an effective amount of the derivative of claim 1, alone or in combination with a pharmaceutical carrier.

8. A method of promoting the endogenous production or release of growth hormone in a subject, comprising administering to the subject an effective amount of the derivative of claim 1, alone or in combination with a pharmaceutical carrier.

9. A method for treating a disease or condition resulting from a growth hormone production abnormality in a subject, comprising administering to the subject an effective amount of the conjugate of claim 3, alone or in combination with a pharmaceutical carrier.

10. A method of promoting the endogenous production or release of growth hormone in a subject comprising administering to the subject an effective amount of the conjugate of claim 3, alone or in combination with a pharmaceutical carrier.

11. The method of claim 7, wherein the subject is a human.

12. The method of claim 8, wherein the subject is a human.

13. The method of claim 9, wherein the subject is a human.

14. The method of claim 10, wherein the subject is a human.

15. The method of claim 7, wherein the subject is a non-human animal.

16. The method of claim 8, wherein the subject is a non-human animal.

17. The method of claim 9, wherein the subject is a non-human animal.

18. The method of claim 10, wherein the subject is a non-human animal.

19. A pharmaceutical composition comprising the conjugate of claim 2 in combination with a pharmaceutical carrier.

20. A pharmaceutical composition comprising the conjugate of claim 3 in combination with a pharmaceutical carrier.

* * * * *

UNITED STATES PATENT AND TRADEMARK OFFICE
CERTIFICATE OF CORRECTION

PATENT NO. : 7,268,113 B2  Page 1 of 1
APPLICATION NO. : 10/203809
DATED : September 11, 2007
INVENTOR(S) : Bridon et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (191) days Delete the phrase "by 191days" and insert -- by 206 days --

Signed and Sealed this

Nineteenth Day of August, 2008

JON W. DUDAS
*Director of the United States Patent and Trademark Office*

SEQUENCE LISTING

```
<160> NUMBER OF SEQ ID NOS: 5

<210> SEQ ID NO 1
<211> LENGTH: 30
<212> TYPE: PRT
<213> ORGANISM: Artificial Sequence
<220> FEATURE:
<223> OTHER INFORMATION: GRF peptide derivative
<220> FEATURE:
<221> NAME/KEY: VARIANT
<222> LOCATION: (1)...(0)
<223> OTHER INFORMATION: Xaa = Tyr, N-Ac-Tyr, His, 3-MeHis, desNH2 His,
      desNH2 Tyr, Lys-Tyr, Lys-His or Lys-3-MeHis
<220> FEATURE:
<221> NAME/KEY: VARIANT
<222> LOCATION: (2)...(0)
<223> OTHER INFORMATION: Xaa = Val, Leu, Ile, Ala, D-Ala, N-methyl-D-Ala,
      (N-methyl)-Ala, Gly, Nle ou Nval
<220> FEATURE:
<221> NAME/KEY: VARIANT
<222> LOCATION: (4)...(0)
<223> OTHER INFORMATION: Xaa = Ala or Gly
<220> FEATURE:
<221> NAME/KEY: VARIANT
<222> LOCATION: (5)...(0)
<223> OTHER INFORMATION: Xaa = Met or Ile
<220> FEATURE:
<221> NAME/KEY: VARIANT
<222> LOCATION: (7)...(0)
<223> OTHER INFORMATION: Xaa = Asn, Ser or Thr
<220> FEATURE:
<221> NAME/KEY: VARIANT
<222> LOCATION: (8)...(0)
<223> OTHER INFORMATION: Xaa = Asn, Gln, Lys or Ser
<220> FEATURE:
<221> NAME/KEY: VARIANT
<222> LOCATION: (9)...(0)
<223> OTHER INFORMATION: Xaa = Ala or Ser
<220> FEATURE:
<221> NAME/KEY: VARIANT
<222> LOCATION: (11)...(0)
<223> OTHER INFORMATION: Xaa = Arg, D-Arg, Lys or D-Lys
```

```
<220> FEATURE:
<221> NAME/KEY: VARIANT
<222> LOCATION: (12)...(0)
<223> OTHER INFORMATION: Xaa = Lys, (N-Me)Lys, or D-Lys
<220> FEATURE:
<221> NAME/KEY: VARIANT
<222> LOCATION: (13)...(0)
<223> OTHER INFORMATION: Xaa = Val or Leu
<220> FEATURE:
<221> NAME/KEY: VARIANT
<222> LOCATION: (15)...(0)
<223> OTHER INFORMATION: Xaa = Ala, Leu or Gly
<220> FEATURE:
<221> NAME/KEY: VARIANT
<222> LOCATION: (18)...(0)
<223> OTHER INFORMATION: Xaa = Ser or Thr
<220> FEATURE:
<221> NAME/KEY: VARIANT
<222> LOCATION: (20)...(0)
<223> OTHER INFORMATION: Xaa = Arg, D-Arg, Lys or D-Lys
<220> FEATURE:
<221> NAME/KEY: VARIANT
<222> LOCATION: (21)...(0)
<223> OTHER INFORMATION: Xaa = Lys, (N-Me)Lys, or Asn
<220> FEATURE:
<221> NAME/KEY: VARIANT
<222> LOCATION: (22)...(0)
<223> OTHER INFORMATION: Xaa = Tyr or Leu
<220> FEATURE:
<221> NAME/KEY: VARIANT
<222> LOCATION: (24)...(0)
<223> OTHER INFORMATION: Xaa = Gln or His
<220> FEATURE:
<221> NAME/KEY: VARIANT
<222> LOCATION: (25)...(0)
<223> OTHER INFORMATION: Xaa = Ser or Asp
<220> FEATURE:
<221> NAME/KEY: VARIANT
<222> LOCATION: (26)...(0)
<223> OTHER INFORMATION: Xaa = Leu or Ile
<220> FEATURE:
<221> NAME/KEY: VARIANT
<222> LOCATION: (27)...(0)
<223> OTHER INFORMATION: Xaa = Met, Ile, Leu or Nle
<220> FEATURE:
<221> NAME/KEY: VARIANT
<222> LOCATION: (28)...(0)
<223> OTHER INFORMATION: Xaa = Ser, Asn, Ala or Asp
<220> FEATURE:
<221> NAME/KEY: VARIANT
<222> LOCATION: (29)...(0)
<223> OTHER INFORMATION: Xaa = Lys or Arg
<220> FEATURE:
<221> NAME/KEY: VARIANT
<222> LOCATION: (30)...(0)
<223> OTHER INFORMATION: Xaa = absent, X, or X-Lys wherein X is absent
      or is the sequence Gln-Gln-Gly-Glu-Ser-Asn-Gln
      -Glu-Arg-Gly-Ala-Arg-Ala-Arg-Leu or a fragment
      thereof

<400> SEQUENCE: 1

Xaa Xaa Asp Xaa Xaa Phe Xaa Xaa Xaa Tyr Xaa Xaa Xaa Leu Xaa Gln
 1               5                  10                  15

Leu Xaa Ala Xaa Xaa Xaa Leu Xaa Xaa Xaa Xaa Xaa Xaa
            20                  25                  30

<210> SEQ ID NO 2
<211> LENGTH: 29
<212> TYPE: PRT
<213> ORGANISM: Artificial Sequence
<220> FEATURE:
<223> OTHER INFORMATION: GRF peptide derivative
<220> FEATURE:
<221> NAME/KEY: AMIDATION
<222> LOCATION: (29)...(0)
```

```
<400> SEQUENCE: 2

Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg
            20                  25

<210> SEQ ID NO 3
<211> LENGTH: 30
<212> TYPE: PRT
<213> ORGANISM: Artificial Sequence
<220> FEATURE:
<223> OTHER INFORMATION: GRF peptide derivative
<220> FEATURE:
<221> NAME/KEY: VARIANT
<222> LOCATION: (30)...(0)
<223> OTHER INFORMATION: MPA attached to the Lys residue
<220> FEATURE:
<221> NAME/KEY: AMIDATION
<222> LOCATION: (30)...(0)

<400> SEQUENCE: 3

Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg Lys
            20                  25                  30

<210> SEQ ID NO 4
<211> LENGTH: 29
<212> TYPE: PRT
<213> ORGANISM: Artificial Sequence
<220> FEATURE:
<223> OTHER INFORMATION: GRF peptide derivative
<220> FEATURE:
<221> NAME/KEY: VARIANT
<222> LOCATION: (1)...(0)
<223> OTHER INFORMATION: N-MPA attached to the Tyr residue
<220> FEATURE:
<221> NAME/KEY: AMIDATION
<222> LOCATION: (29)...(0)

<400> SEQUENCE: 4

Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg
            20                  25

<210> SEQ ID NO 5
<211> LENGTH: 29
<212> TYPE: PRT
<213> ORGANISM: Artificial Sequence
<220> FEATURE:
<223> OTHER INFORMATION: GRF peptide derivative
<220> FEATURE:
<221> NAME/KEY: VARIANT
<222> LOCATION: (1)...(0)
<223> OTHER INFORMATION: N-AEEA-MPA attached to the Tyr residue
<220> FEATURE:
<221> NAME/KEY: AMIDATION
<222> LOCATION: (29)...(0)

<400> SEQUENCE: 5

Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg
            20                  25
```